(12) United States Patent
Wentland

(10) Patent No.: US 8,957,085 B2
(45) Date of Patent: Feb. 17, 2015

(54) CARBOXAMIDE BIOISOSTERES OF OPIATES

(71) Applicant: Rensselaer Polytechnic Institute, Troy, NY (US)

(72) Inventor: Mark P. Wentland, Watervliet, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 14/206,170

(22) Filed: Mar. 12, 2014

(65) Prior Publication Data

US 2014/0194457 A1 Jul. 10, 2014

Related U.S. Application Data

(60) Continuation of application No. 13/857,588, filed on Apr. 5, 2013, now Pat. No. 8,716,306, which is a division of application No. 13/069,104, filed on Mar. 22, 2011, now Pat. No. 8,436,175.

(60) Provisional application No. 61/421,915, filed on Dec. 10, 2010, provisional application No. 61/394,148, filed on Oct. 18, 2010, provisional application No. 61/316,175, filed on Mar. 22, 2010.

(51) Int. Cl.
| | | |
|---|---|---|
| *C07D 221/26* | (2006.01) | |
| *A61K 45/06* | (2006.01) | |
| *C07D 489/00* | (2006.01) | |
| *A61K 31/485* | (2006.01) | |
| *A61K 31/4748* | (2006.01) | |
| *C07D 405/12* | (2006.01) | |
| *C07D 221/28* | (2006.01) | |
| *C07D 489/08* | (2006.01) | |
| *A61K 31/439* | (2006.01) | |
| *C07D 221/22* | (2006.01) | |

(52) U.S. Cl.
CPC ............ *C07D 221/26* (2013.01); *C07D 221/28* (2013.01); *C07D 489/08* (2013.01); *A61K 31/439* (2013.01); *A61K 45/06* (2013.01); *C07D 221/22* (2013.01); *A61K 31/4748* (2013.01); *A61K 31/485* (2013.01); *C07D 405/12* (2013.01); *C07D 489/00* (2013.01)
USPC .............. 514/282; 514/295; 514/289; 546/97; 546/46; 546/74

(58) Field of Classification Search
None
See application file for complete search history.

(56) References Cited

U.S. PATENT DOCUMENTS

| | | | |
|---|---|---|---|
| 3,856,795 A | 12/1974 | Yardley | |
| 3,957,793 A | 5/1976 | Wentland et al. | |
| 4,032,529 A | 6/1977 | Wentland et al. | |
| 4,176,186 A | 11/1979 | Goldberg et al. | |
| 4,205,171 A | 5/1980 | Albertson | |
| 4,374,139 A | 2/1983 | Mohacsi | |
| 4,489,079 A | 12/1984 | Giudice et al. | |
| 4,649,200 A | 3/1987 | Portoghese | |
| 4,929,622 A | 5/1990 | Allen et al. | |
| 5,258,386 A | 11/1993 | Newman | |
| 5,607,941 A | 3/1997 | Merz et al. | |
| 6,365,594 B1 | 4/2002 | Dondio et al. | |
| 6,784,187 B2 | 8/2004 | Wentland | |
| 6,812,236 B2 | 11/2004 | Gibson et al. | |
| 7,262,298 B2 | 8/2007 | Wentland | |
| 7,265,226 B2 | 9/2007 | Wentland | |
| 7,557,119 B2 | 7/2009 | Wentland | |
| 2002/0099216 A1 | 7/2002 | Gibson et al. | |
| 2003/0187009 A1 | 10/2003 | Wentland | |
| 2005/0176645 A1 | 8/2005 | Mickle et al. | |
| 2005/0182258 A1 | 8/2005 | Schmidhammer et al. | |
| 2005/0215799 A1 | 9/2005 | Wentland et al. | |

(Continued)

FOREIGN PATENT DOCUMENTS

| | | |
|---|---|---|
| DE | 2254298 | 5/1974 |
| EP | 0254120 | 1/1988 |

(Continued)

OTHER PUBLICATIONS

Wentland et al., "3-Carboxamido Analogues of Morphine and Naltrexone: Synthesis . . . .", Bioorg. Med. Chem. Ltrs. 11, pp. 1717-1721 (2001).

(Continued)

*Primary Examiner* — Janet L Andres
*Assistant Examiner* — Timothy R Rozof
(74) *Attorney, Agent, or Firm* — Heslin Rothenberg Farley & Mesiti P.C.

(57) ABSTRACT

A compound of formula I is disclosed.

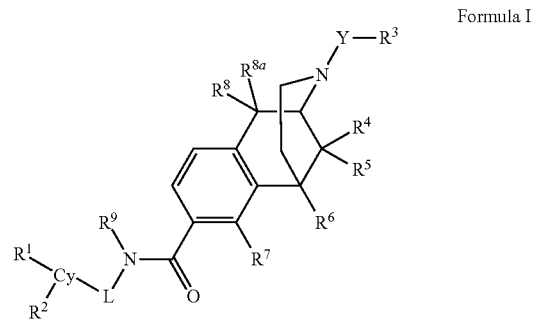

Formula I

Compounds of formula I are useful as analgesics, anti-inflammatory agents, anti-diarrheal agents, anticonvulsants, antitussives and anti-addiction medications.

19 Claims, No Drawings

(56) References Cited

U.S. PATENT DOCUMENTS

| | | |
|---|---|---|
| 2006/0030580 A1 | 2/2006 | Wentland |
| 2007/0021457 A1 | 1/2007 | Wentland |
| 2009/0197905 A1 | 8/2009 | Wentland |
| 2009/0247562 A1 | 10/2009 | Wentland |
| 2010/0130512 A1 | 5/2010 | Wentland |
| 2010/0190817 A1 | 7/2010 | Wentland |

FOREIGN PATENT DOCUMENTS

| | | |
|---|---|---|
| EP | 0632041 | 1/1995 |
| ES | 2121553 | 11/1998 |
| GB | 874217 | 8/1961 |
| GB | 1340720 | 12/1973 |
| JP | 40010154 | 5/1965 |
| WO | 9311761 | 6/1993 |
| WO | 9725331 | 7/1997 |
| WO | 9852929 | 11/1998 |
| WO | 0112197 | 2/2001 |
| WO | 0137785 | 5/2001 |
| WO | 0236573 | 5/2002 |
| WO | 03101963 | 12/2003 |
| WO | 2004005294 | 1/2004 |
| WO | 2004007449 | 1/2004 |
| WO | 2004045562 | 6/2004 |
| WO | 2006052710 | 5/2006 |
| WO | 2006096626 | 9/2006 |
| WO | 2007014137 | 2/2007 |
| WO | 2007022535 | 2/2007 |
| WO | 2008144394 | 1/2008 |
| WO | 2009023567 | 2/2009 |
| WO | 2010011619 | 1/2010 |
| WO | 2011119605 | 9/2011 |

OTHER PUBLICATIONS

Wentland et al., "8-Carboxamidocyclazocine Analogues: Redefining the Structure-Activity . . . .", Bioorg. Med. Chem. Ltrs. 11, pp. 623-626 (2001).
Davies et al., "Palladium Catalysed Elaboration of Codeine and Morphine", J. Chem Soc., Perkin Trans. 1, pp. 1413-1420 (2001).
McCurdy et al., "Investigation of Phenolic Bioisosterism in Opiates: 3-Sulfonamido Analogues of Naltrexone and Oxymorphone", Organic Letters vol. 2, No. 6, pp. 819-821 (2000).
Kubota et al., "Palladium-Catalyzed Cyanation of Hindered, Electron-Rich . . . .", Tetrahedron Ltrs. 39, pp. 2907-2910 (1998).
Kubota et al., "Synthesis and Biological Activity of 3-Substituted . . . .", Bioorg. Med. Chem. Ltrs. 8, pp. 799-804 (1998).
Wentland et al., "8-Aminocyclazocine Analogues: Synthesis and Structure . . . .", Bioorg. Med. Chem. Ltrs. 10, pp. 183-187 (2000).
Wentland et al., "Selective Protection and Functionalization of Morphine . . . .", J. Med. Chem. 43, pp. 3558-3565 (2000).
Danso-Danquah et al., "Synthesis and σ Binding Properties of 2' Substituted", J. Med. Chem. 38, pp. 2978-2985 (1995).
Diaz et al., "SAR & Biological Evaluation of Novel trans-3,4-dimethyl-4-arylpiperidine Derivatives as . . . .", Bioorganic & Medicinal Chemistry Letters 15, pp. 3844-3848 (2005).
Ida, "The Nonnarcotic Antitussive Drug Dimemorfan: A Review", Clinical Therapeutics, vol. 19, No. 2, pp. 215-231 (1997).
Morera et al., "A Palladium-Catalyzed Carbonylative Route to Primary Amides", Tetrahedron Ltrs. 39, pp. 2835-2838 (1998).
Jendralla et al., "Efficient Kg-Scale Synthesis of Thrombin Inhibitor CRC 220", Tetrahedron vol. 51, No. 44, pp. 12047-12068 (1995).
Cacchi et al., "Palladium-Catalyzed Carbonylation of Aryl Triflates", Tetrahedron Ltrs. 27, pp. 3931-3934 (1986).
Varma et al., "Microwave-Accelerated Solvent-Free Synthesis of Thioketones, Thiolactones, Thioamides, Thionoesters, and Thioflavonoids", Organic Letters, vol. 1, No. 5, pp. 697-700 (1999).
Dorwald, "Side Reactions in Organic Synthesis", Wiley-VCH, Weinheim p. IX of Preface (2005).
International Preliminary Examination Report for PCT/US01/45581, date of completion Feb. 5, 2003.
International Search Report for PCT/US01/45581, date of completion Jul. 30, 2002.
Vanalstine, "Design Synthesis and Evaluation of Novel n-Substituted Derivatives of 8-Carboxamidocyclazocine", Rensselaer Polytechnic Institute, pp. i-202, May 2007. Available online on Jul. 9, 2009.
Wentland et al., "Redefining the Structure-Activity Relationships of 2,6-methano-3-benzazocines. 4. Opioid Receptor Binding Properties of 8-[N-(4'-phenyl)-phenethyl) carboxamidol] Analogues of Cyclazocine and Ethylketocyclazocine", Journal of Medicinal Chemistry, vol. 49, No. 18, pp. 5635-5639, XP002550099, Sep. 7, 2006.
Vanalstine et al., "Redefining the Structure-Activity Relationships of 2,6-methano-3-benzazocines. 5. Opioid Receptor Binding Properties of N-((4"-phenyl)-phenethyl) Analogues of 8-CAC", Bioorganic & Medicinal Chemistry Letters, Pergamon, Elsevier Science, GB. vol. 17, No. 23, pp. 6516-6520, XP022325927, Nov. 2, 2007.
International Search Report and Written Opinion for PCT/US2009/051200, mailed Nov. 11, 2009.
Wentland et al., "Syntheses and Opioid Receptor Binding Affinities of 8-Amino-2, 6-methano-3-benzazocines", Journal of Medicinal Chemistry, vol. 46, No. 5, pp. 838-849 (2003).
Wentland et al., "Redefining the Structure-Activity Relationships of 2, 6-methano-3-benzazocines. Part 6: Opioid Receptor Binging Properties of Cyclic Variants of 8-Carboxamidocyclazocine", Bioorganic & Medicinal Chemistry, vol. 16, No. 10, pp. 5653-5664, (2008).
International Search Report and Written Opinion for PCT/US2008/063713, mailed May 28, 2009.
Wentland et al., "Redefining the Structure-Activity Relationships of 2,6-methano-3-benzazocines. Part 3: 8-Thiocarbozamido and 8-Thioformamido Derivatives of Cyclazocine", Bioorg. Med. Chem. Lett. 15(10), pp. 2547-2551 (2005).
Wentland et al., "Synthesis and Opioid Receptor Binding Properties of a Highly Potent 4-Hydroxy Analogue of Naltrexone", Bioorg. Med. Chem. Lett. 15(8), pp. 2107-2110 (2005).
International Search Report for PCT/US2006/028634, mailed Jan. 26, 2007.
International Search Report for PCT/US2005/039911, date completed Apr. 19, 2006.
International Search Report and Written Opinion for PCT/US2008/072632, mailed Dec. 23, 2008.
International Search Report and Written Opinion for PCT/US2011/029425, mailed Sep. 16, 2011.
Mohacsi et al., "Acylmorphinans. A Novel Class of Potent Analgesic Agents", J. Med. Chem., pp. 1177-1180 (1985).
Coop et al., "Opioid Affinity and Selectivity of 4-Hydroxy-3-Methoxyindolomorphinan Analogues Related to Naltrindole", J. Med. Chem 42, pp. 1673-1679 (1999).
Bhargava, "Synthesis of 2'-Amino-17-cyclopropylmethyl-6,7-dehydro-3,14-dihy-droxy-4,5α-epoxy-6,7:4',5'-thiazolomorphinan from Naltrexone [1]", J. Heterocyclic Chem., 34, pp. 1195-1203 (1997).
Coop et al., "Direct and Simple Conversion of Codeine to Thebainone-A and Dihydrothebainone", Heterocycles, vol. 50, No. 1, pp. 39-42 (1999).
Neumeyer et al., "Design and Synthesis of Novel Dimeric Morphinan Ligands for κ and μ Opioid Receptors", J. Med Chem. 46, pp. 5162-5170 (2003).
Bianchi et al., "Quaternary Narcotic Antagonists' Relative Ability to Prevent Antinociception and Gastrointestinal Transit Inhibition in Morphine-Treated Rats as an Index of Peripheral Selectivity", Life Sciences 30(22), pp. 1875-1883 (1982).
Huidobro-Toro et al., "Comparative Study on the Effect of Morphine and the Opioid-Like Peptides in the Vas Deferens of Rodents: Species and Strain Differences, Evidence for Multiple Opiate Receptors", Life Sciences, vol. 28, pp. 1331-1336 (1981).
Simpkins et al., "Evaluation of the Sites of Opioid Influence on Anterior Pituitary Hormone Secretion Using a Quaternary Opiate Antagonist", Neuroendocrinology 54(4), pp. 384-390 (1991).
Bianchetti et al., "Quaternary Derivatives of Narcotic Antagonists: Stereochemical Requirements at the Chiral Nitrogen for In Vitro and In Vivo Activity", Life Sciences 33(Suppl. 1), pp. 415-418 (1983).

(56) References Cited

OTHER PUBLICATIONS

Written Opinion in PCT/US2005/039911, completed Apr. 19, 2006.
IPRP for PCT/US2006/028634, issued Jan. 22, 2008.
Zhang et al., "10-Ketomorphinan and 3-Substituted 3-desoxymorphinan Analogues as Mixed κ and μ Opioid Ligands: Synthesis and Biological Evaluation of Their Binding Affinity at Opioid Receptors", J. Med. Chem. 47, pp. 165-174 (2004).
CAS Registry No. 1028267-07-3; STN Entry Date: Jun. 15, 2008.
CAS Registry No. 1027570-82-6; STN Entry Date: Jun. 12, 2008.
CAS Registry No. 1027414-05-6; STN Entry Date: Jun. 11, 2008.
CAS Registry No. 1027033-50-6; STN Entry Date: Jun. 10, 2008.
CAS Registry No. 1026857-16-8; STN Entry Date: Jun. 10, 2008.
CAS Registry No. 1026033-14-6; STN Entry Date: Jun. 6, 2008.

CARBOXAMIDE BIOISOSTERES OF OPIATES

CROSS REFERENCE TO RELATED APPLICATIONS

This application is a continuation application of U.S. patent application Ser. No. 13/857,588, filed Apr. 5, 2013, now allowed, which is a divisional application of U.S. patent application Ser. No. 13/069,104, filed Mar. 22, 2011, now U.S. Pat. No. 8,436,175. U.S. patent application Ser. No. 13/069,104 claims priority of U.S. provisional applications 61/316,175, filed Mar. 22, 2010, 61/394,148, filed Oct. 18, 2010, and 61/421,915, filed Dec. 10, 2010. The entire contents of each of the prior applications are hereby incorporated herein by reference.

FEDERALLY SPONSORED RESEARCH

The following invention was made with Government support under contract number R01 DA12180 awarded by U.S. Dept of Health and Human Services. The Government has certain rights in this invention.

FIELD OF THE INVENTION

The invention relates to opioid receptor binding compounds containing carboxamides that have large substituents on the nitrogen of the carboxamide. The compounds are useful as analgesics, anti-diarrheal agents, anticonvulsants, anti-obesity agents, antitussives, anti-cocaine, anti-inflammatory, and anti-addiction medications.

BACKGROUND OF THE INVENTION

Opiates have been the subject of intense research since the isolation of morphine in 1805, and thousands of compounds having opiate or opiate-like activity have been identified. Many opioid receptor-interactive compounds including those used for producing analgesia (e.g., morphine) and those used for treating drug addiction (e.g., naltrexone and cyclazocine) in humans have limited utility due to poor oral bioavailability and a very rapid clearance rate from the body. This has been shown in many instances to be due to the presence of the 8-hydroxyl group (OH) of 2,6-methano-3-benzazocines, also known as benzomorphans [(e.g., cyclazocine and EKC (ethylketocyclazocine)] and the corresponding 3-OH group in morphinans (e.g., morphine). Furthermore, charts 1-3 depicts a set of opiate binding compounds that are used to treat diseases mediated by opiate receptors.

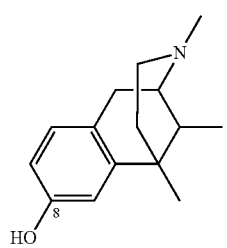

benzomorphan numbering

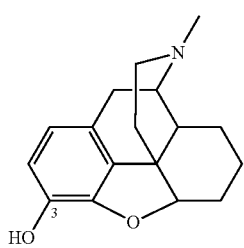

morphinan numbering

Chart 1. Opioid Receptor Ligands
Benzomorphinans (a.k.a. 2,6-Methano-3-benzazocines)

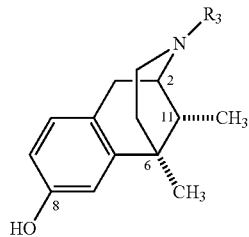

Cyclazocine, $R_3 = CH_2\text{-}\underline{c}\text{-}C_3H_5$
Metazocine, $R_3 = CH_3$
Phenazocine, $R_3 = CH_2C_6H_5$
SKF 10,047, $R_3 = CH_2CH=CH_2$
Pentazocine, $R_3 = CH_2CH=C(CH_3)_2$
(all racemic)

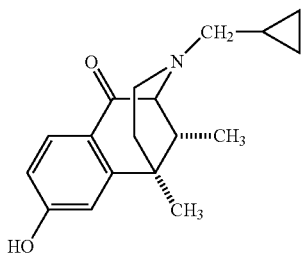

Ketocyclazocine

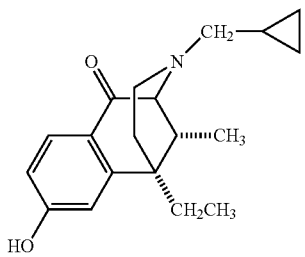

Ethylketocyclazocine (EKC)

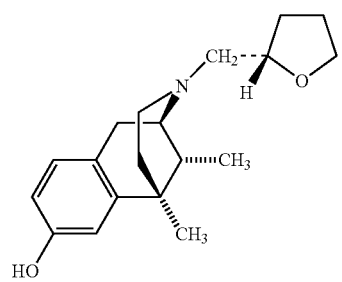

MR2034 - "Merz" core structure (opt. active)

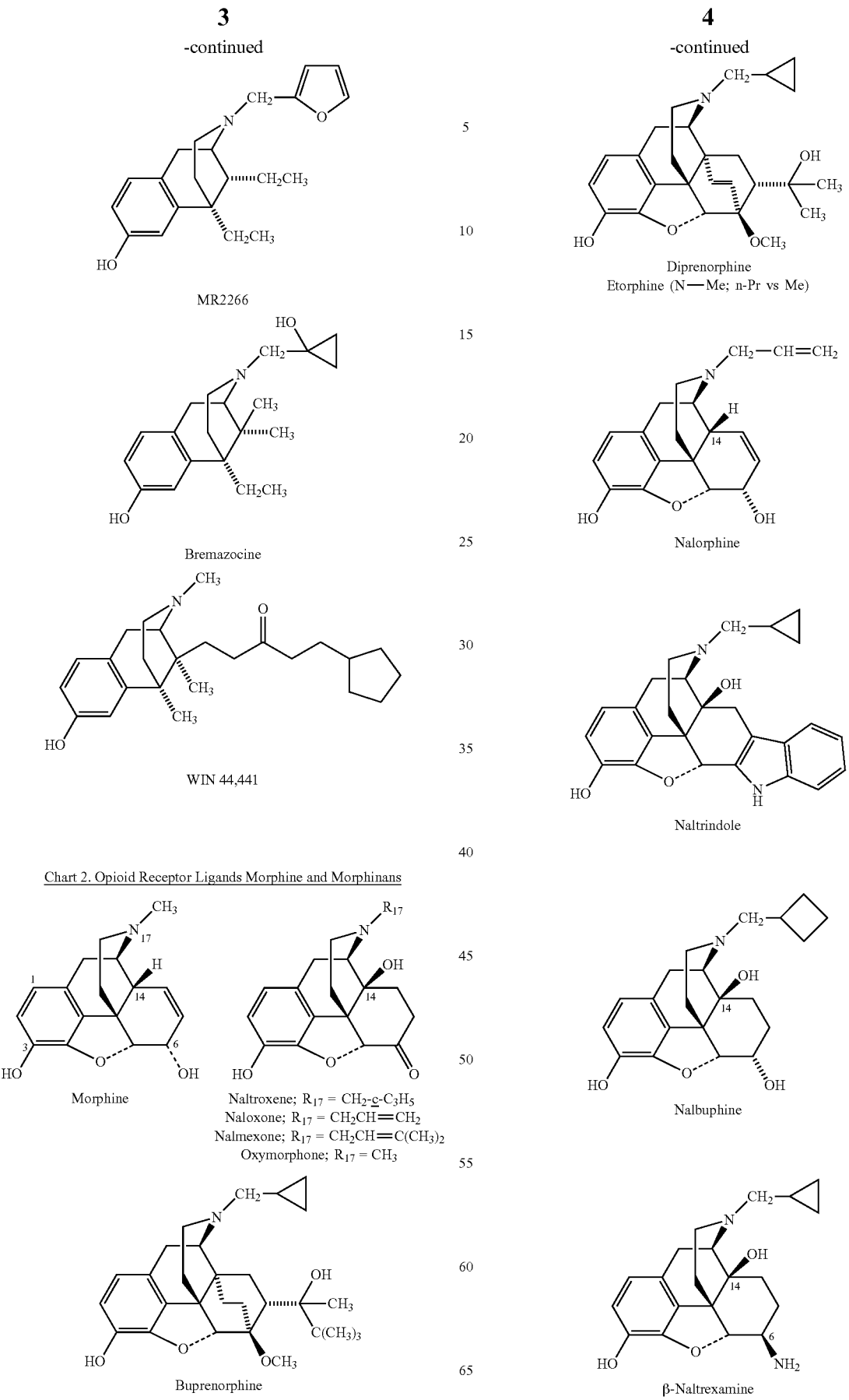

-continued

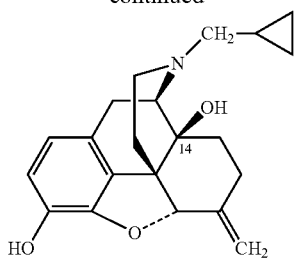

Nalmefene

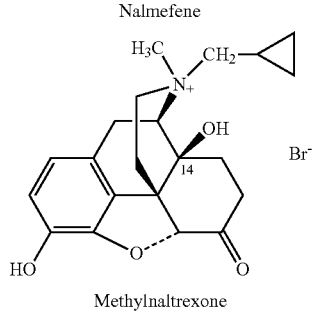

Methylnaltrexone

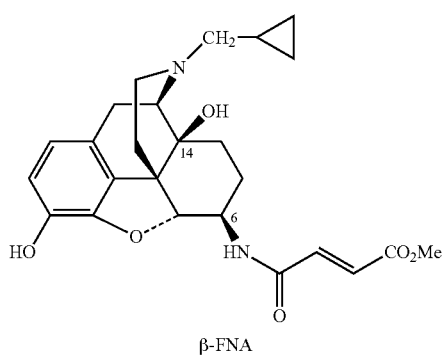

β-FNA

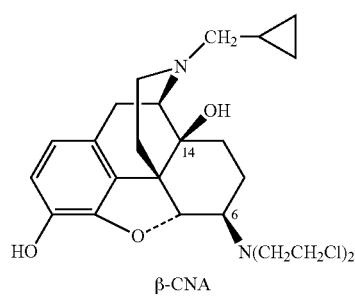

β-CNA

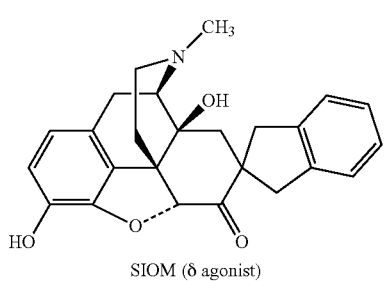

SIOM (δ agonist)

-continued

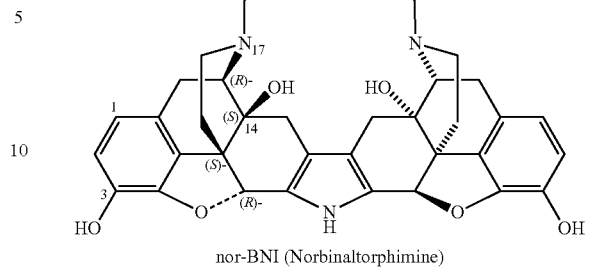

nor-BNI (Norbinaltorphimine)
Reg # = 105618-26-6

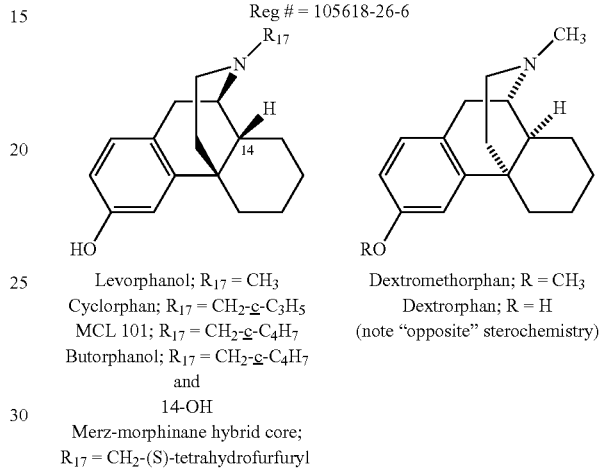

Levorphanol; $R_{17}$ = $CH_3$
Cyclorphan; $R_{17}$ = $CH_2$-c-$C_3H_5$
MCL 101; $R_{17}$ = $CH_2$-c-$C_4H_7$
Butorphanol; $R_{17}$ = $CH_2$-c-$C_4H_7$
and
14-OH
Merz-morphinane hybrid core;
$R_{17}$ = $CH_2$-(S)-tetrahydrofurfuryl Dextromethorphan; R = $CH_3$
Dextrorphan; R = H
(note "opposite" sterochemistry)

Chart 3- Miscellaneous Opioid Receptor Ligands

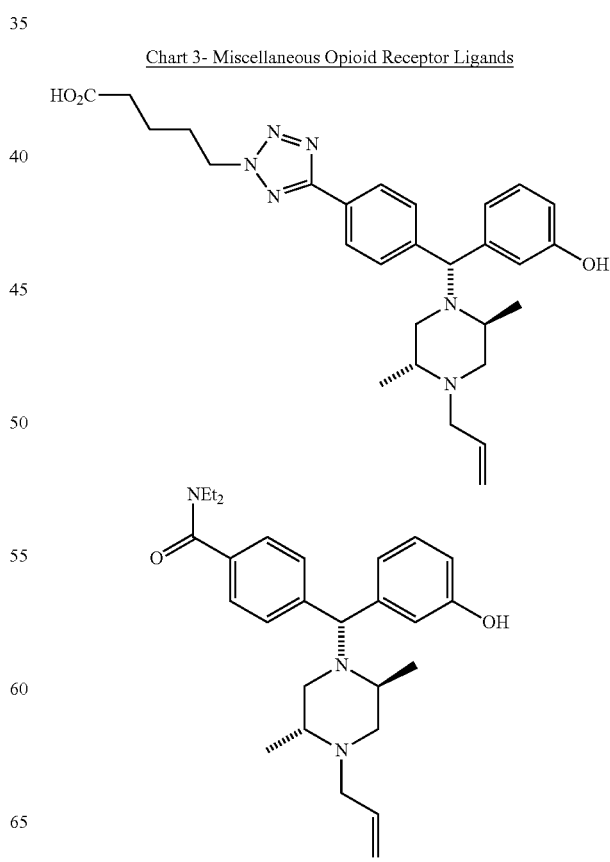

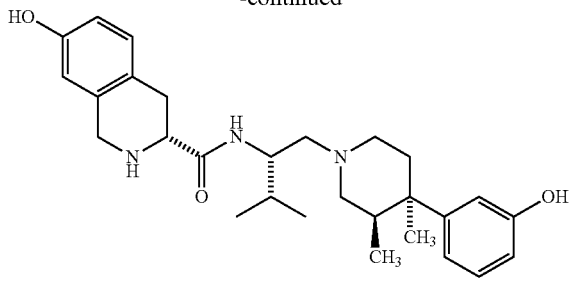

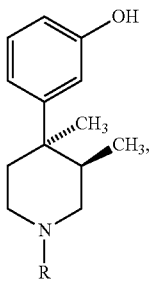

wherein, R is selected from $CH_3$, $CH_2CH_2CH(OH)C_6H_{11}$, $CH_2CH(CH_2Ph)CONHCH_2CO_2H$, $(CH_2)_3CH(CH_3)_2$, and $(CH_2)_3$-2-thienyl,

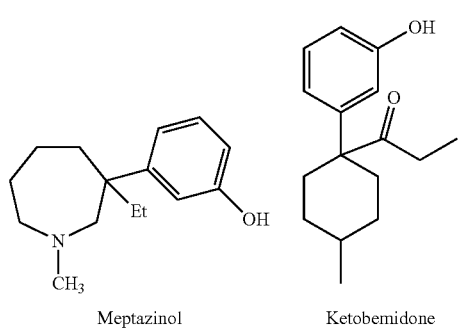

Meptazinol    Ketobemidone

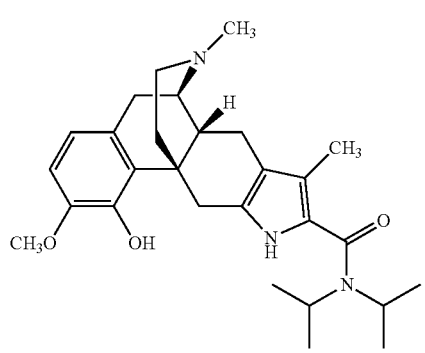

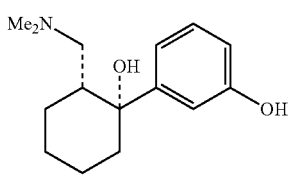

Tramadol active metabolite
Registry Number 80456-81-1

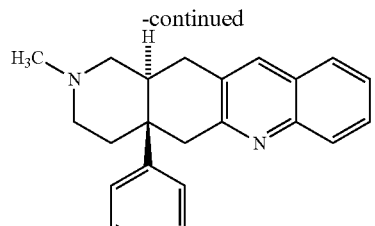

(+)-TAN 67

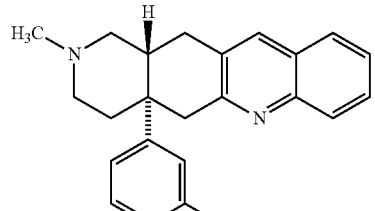

(−)-TAN 67

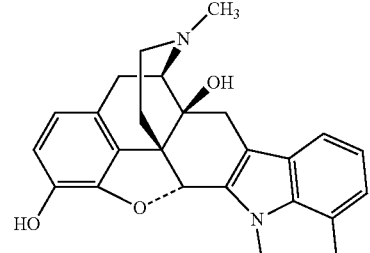

Other opioid receptor ligands are described in Aldrich, J. V. "Analgesics" in *Burger's Medicinal Chemistry and Drug Discovery*, M. E. Wolff ed., John Wiley & Sons 1996, pages 321-44, the disclosures of which are incorporated herein by reference.

The high polarity of these hydroxyl groups retards oral absorption of the parent molecules. Furthermore, the 8-(or 3-)OH group is prone to sulfonation and glucuronidation (Phase II metabolism), both of which facilitate rapid excretion of the active compounds, leading to disadvantageously short half-lives for the active compounds. Until the publications of Wentland in 2001, the uniform experience in the art of the past seventy years had been that removal or replacement of the 8-(or 3-)OH group had led to pharmacologically inactive compounds.

U.S. Pat. No. 6,784,187 (to Wentland) disclosed that the phenolic OH of opioids could be replaced by $CONH_2$. In the cyclazocine series of opioids, it was shown that 8-carboxamidocyclazocine (8-CAC) had high affinity for μ and κ opioid receptors. In studies in vivo, 8-CAC showed high antinociception activity and a much longer duration of action than cyclazocine (15 h vs. 2 h) when both were dosed at 1 mg/kg ip in mice. Preliminary structure-activity relationship studies for 8-CAC revealed that mono-substitution of the carboxamide nitrogen with methyl or phenyl reduced binding affinity for guinea pig μ receptors 75- and 2313-fold, respectively whereas dimethylation of the carboxamide group reduced binding affinity 9375-fold. The finding that substitution of the carboxamide nitrogen had such a detrimental effect suggested that the $NH_2$ of the amide was critical to opioid binding.

We recently reported that the nitrogen of the carboxamide can be substituted with fairly large and relatively non-polar groups, and that such compounds exhibit good opioid binding and, presumably, good metabolic stability. (WO 2010/011619) Compounds with improved activity can be used to reduce dosage, side effects and costs.

SUMMARY OF THE INVENTION

In one aspect, the invention relates to compounds of formula I:

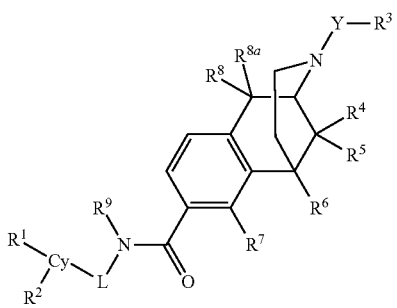

wherein $R^1$ and $R^2$ are each independently selected from hydrogen, halogen, —OH, —CN, —CHO, —OCH$_3$, —OCH$_2$CH$_3$, —OCH(CH$_3$)$_2$, —NO$_2$, —COR$^{10}$, —COOR$^{10}$, —SO$_2$R$^{10}$, —CONR$^{10}$R$^{11}$, —CSNR$^{10}$R$^{11}$, —CONR$^{10}$NR$^{11}$R$^{12}$, —CONR$^{10}$OR$^{11}$, —CONR$^{10}$((C(R$^{12}$)(R$^{13}$))$_t$CONR$^{10}$R$^{11}$, —CONR$^{10}$((C(R$^{12}$)(R$^{13}$))$_t$COOR$^{11}$, —C(=S)R$^{10}$, —C(=NOR$^{11}$)R$^{10}$, C(=NR$^{10}$)R$^{11}$, —SO$_2$NR$^{10}$R$^{11}$, heterocyclyl, optionally substituted lower alkyl, optionally substituted alkenyl, optionally substituted alkynyl, optionally substituted aryl, halo(C$_1$-C$_6$)alkyl, halo(C$_1$-C$_6$)alkoxy, and (C$_1$-C$_6$)alkylthio;

or, $R^1$ and $R^2$ together with the atoms to which they are attached, and a fragment selected from —OCH$_2$O—, or —OCH$_2$CH$_2$O—, form a ring, wherein when Cy is an aromatic group $R^1$ and $R^2$ cannot both be hydrogen;

wherein when Cy is an aromatic group $R^1$ and $R^2$ cannot both be halogen;

$R^3$ is chosen from hydrogen, C$_1$-C$_8$ hydrocarbon, heterocyclyl, aryl and hydroxyalkyl;

$R^4$ is chosen from hydrogen, hydroxyl, amino, lower alkoxy, C$_1$-C$_{20}$ alkyl and C$_1$-C$_{20}$ alkyl substituted with hydroxyl or carbonyl;

$R^5$ is lower alkyl;

$R^6$ is lower alkyl;

$R^7$ is chosen from hydrogen, NR$^{10}$R$^{11}$ and —OR$^{10}$; or together $R^4$, $R^5$, $R^6$ and $R^7$ may form from one, two, three, or four rings, said rings having optional additional substitution;

$R^8$ and $R^{8a}$ are both hydrogen or taken together $R^8$ and $R^{8a}$ are =O;

$R^9$ is chosen from hydrogen and lower alkyl;

$R^{10}$, $R^{11}$, $R^{12}$ and $R^{13}$ are each independently hydrogen, optionally substituted lower alkyl, optionally substituted alkenyl, optionally substituted alkynyl, optionally substituted aryl, hydroxyl, —NR$^{100}$R$^{101}$ or optionally substituted lower alkoxy, or $R^{10}$ and $R^{11}$, together with the nitrogen atom to which they are attached, form an optionally substituted fused carbocyclic or heterocyclic ring having from 5 to 7 ring members of which up to 3 can be heteroatoms selected from N, O and S;

t is 0, 1, 2, 3, 4, 5, or 6;

$R^{100}$ and $R^{101}$ are each independently hydrogen, optionally substituted lower alkyl, optionally substituted alkenyl, optionally substituted alkynyl, optionally substituted aryl, hydroxyl, or optionally substituted lower alkoxy, or $R^{100}$ and $R^{101}$, together with the nitrogen atom to which they are attached, form an optionally substituted fused carbocyclic or heterocyclic ring having from 5 to 7 ring members of which up to 3 can be heteroatoms selected from N, O and S;

Y is a direct bond or —(C(R$^{10}$)(R$^{11}$))q-, wherein q is 0, 1, 2, 3, 4 or 5;

L is a direct bond or —(C(R$^{10}$)(R$^{11}$))q-; and

Cy is Ar$^1$—B—Ar$^2$, wherein

Ar$^1$ is absent, or an aryl or heteroaryl radical having from 1 to 4 N, O and/or S atoms, which may be unsubstituted or mono-, di- or trisubstituted by halogen, lower alkyl, alkenyl, alkynyl, cycloalkyl, —OR$^{10}$, —NR$^{10}$R$^{11}$, —CN, —COR$^{10}$ or —COOR$^{10}$;

B is a direct bond, —O—, —NR$^{10}$, —SO$_2$, or —(C(R$^{10}$)(R$^{11}$))$_s$—, wherein s is 0, 1, 2, 3, 4 or 5; and Ar$^2$ is aryl or heteroaryl radical having from 1 to 4 N, O and/or S atoms, which may be unsubstituted or mono-, di- or trisubstituted by halogen, lower alkyl, alkenyl, alkynyl, cycloalkyl, —OR$^{10}$, —NR$^{10}$R$^{11}$, —CN, —COR$^{10}$ or —COOR$^{10}$, wherein when Cy is phenyl or biphenyl, $R_1$ is other than —OCH$_3$.

In another aspect, the invention relates to compounds of formula Ia:

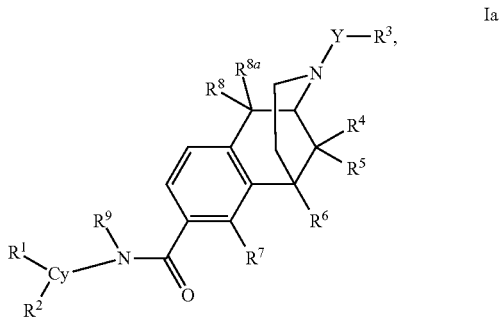

wherein L is a direct bond, and all other substituents are defined as above.

In one aspect of the invention, the compounds described in charts 1-3 are substituted at the phenolic hydroxyl position. For instance, compounds of charts 1-3 are substituted at the phenolic hydroxyl position with —C(O)N(R$^9$)LCy(R$^1$)(R$^2$), wherein the carboxamido moiety replaces the hydroxyl group to give a compound of formula I or formula Ia.

In another aspect, the invention relates to a pharmaceutical formulation comprising a compound of formula I or formula Ia and a pharmaceutically acceptable carrier.

In another aspect, the invention relates to a method of preventing or treating a condition or disease associated with binding opioid receptors in a patient in need thereof, comprising the step of administering to said patient a composition comprising an effective amount of a compound of formula I or formula Ia.

The compounds of the invention are therefore useful as analgesics, anti-inflammatory agents, anti-pruritics, anti-diarrheal agents, anticonvulsants, antitussives, anorexics and as treatments for hyperalgesia, anti-addiction, respiratory depression, dyskinesia, pain (including neuropathic pain), irritable bowel syndrome and gastrointestinal motility disorders. As used herein, anti-addition medications can be used interchangeably with the term drug addiction, which includes alcohol, cocaine, heroin, amphetamine and nicotine addiction. There is evidence in the literature that the compounds may also be useful as immunosuppressants and antiinflammatories and for reducing ischemic damage (and cardioprotection), for improving learning and memory, and for treating urinary incontinence. In particular, the compounds of the invention are useful for the treatment of osteoarthritis.

In another aspect, the invention relates to a method of preventing or treating a condition or disease associated with binding opioid receptors in a patient in need thereof, comprising the step of administering to said patient a composition comprising an effective amount of a compound of formula I or formula Ia. In further embodiments, drug addiction encompasses heroin, cocaine, amphetamine, nicotine or alcohol addiction. In other embodiments, the condition is pain and the composition further comprises an effective amount of an opioid. In yet a further embodiment, the condition is osteoarthritis and the composition further comprises an effective amount of an opioid.

DETAILED DESCRIPTION OF THE INVENTION

From many years of SAR studies, it is known that the hydroxyl of morphinans and benzomorphans interacts with a specific site in the opiate receptor. Our recent studies have found that the hydroxyl can be replaced with a carboxamide residue. A fairly wide range of secondary carboxamides exhibits binding in the desired range below 25 nanomolar. We recently reported a set of compounds with cyclic groups attached at the carboxamide position. (US 20070021457, WO 2010/011619, and Ser. No. 12/506,354, the entire contents of which are incorporated by reference herein). It has been surprisingly found that a selected groups of substituents on the cyclic group provides significantly improved binding properties.

In one aspect the invention relates to compounds of formula I:

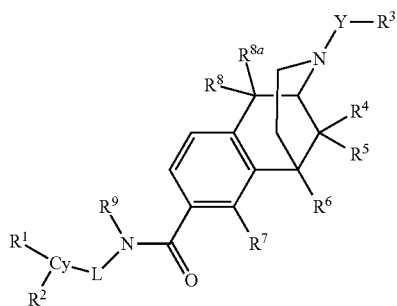

I wherein $R^1$ and $R^2$ are each independently selected from hydrogen, halogen, —OH, —CN, —CHO, —OCH$_3$, —OCH$_2$CH$_3$, —OCH(CH$_3$)$_2$, —NO$_2$, —COR$^{10}$, —COOR$^{10}$, —SO$_2$R$^{10}$, —CONR$^{10}$R$^{11}$, —CSNR$^{10}$R$^{11}$, —CONR$^{10}$NR$^{11}$R$^{12}$, —CONR$^{10}$OR$^{11}$, —CONR$^{10}$((C(R$^{12}$)(R$^{13}$),CONR$^{10}$R$^{11}$, —CONR$^{10}$((C(R$^{12}$)(R$^{13}$),COOR$^{11}$, —C(=S)R$^{10}$, —C(=NOR$^{11}$)R$^{10}$, C(=NR$^{10}$)R$^{11}$, —SO$_2$NR$^{10}$R$^{11}$, heterocyclyl, optionally substituted lower alkyl, optionally substituted alkenyl, optionally substituted alkynyl, optionally substituted aryl, halo(C$_1$-C$_6$)alkyl, halo(C$_1$-C$_6$)alkoxy, and (C$_1$-C$_6$)alkylthio;

or, $R^1$ and $R^2$ together with the atoms to which they are attached, and a fragment selected from —OCH$_2$O—, or —OCH$_2$CH$_2$O—, form a ring, wherein when Cy is an aromatic group $R^1$ and $R^2$ cannot both be hydrogen;

wherein when Cy is an aromatic group $R^1$ and $R^2$ cannot both be halogen;

$R^3$ is chosen from hydrogen, C$_1$-C$_8$ hydrocarbon, heterocyclyl, aryl and hydroxyalkyl;

$R^4$ is chosen from hydrogen, hydroxyl, amino, lower alkoxy, C$_1$-C$_{20}$ alkyl and C$_1$-C$_{20}$ alkyl substituted with hydroxyl or carbonyl;

$R^5$ is lower alkyl;

$R^6$ is lower alkyl;

$R^7$ is chosen from hydrogen, NR$^{10}$R$^{11}$ and —OR$^{10}$; or together $R^4$, $R^5$, $R^6$ and $R^7$ may form from one, two, three, or four rings, said rings having optional additional substitution;

$R^8$ and $R^{8a}$ are both hydrogen or taken together $R^8$ and $R^{8a}$ are =O;

$R^9$ is chosen from hydrogen and lower alkyl;

$R^{10}$, $R^{11}$, $R^{12}$ and $R^{13}$ are each independently hydrogen, optionally substituted lower alkyl, optionally substituted alkenyl, optionally substituted alkynyl, optionally substituted aryl, hydroxyl, —NR$^{100}$R$^{101}$ or optionally substituted lower alkoxy, or $R^{10}$ and $R^{11}$, together with the nitrogen atom to which they are attached, form an optionally substituted fused carbocyclic or heterocyclic ring having from 5 to 7 ring members of which up to 3 can be heteroatoms selected from N, O and S;

t is 0, 1, 2, 3, 4, 5, or 6;

$R^{100}$ and $R^{101}$ are each independently hydrogen, optionally substituted lower alkyl, optionally substituted alkenyl, optionally substituted alkynyl, optionally substituted aryl, hydroxyl, or optionally substituted lower alkoxy, or $R^{100}$ and $R^{101}$, together with the nitrogen atom to which they are attached, form an optionally substituted fused carbocyclic or heterocyclic ring having from 5 to 7 ring members of which up to 3 can be heteroatoms selected from N, O and S;

Y is a direct bond or —(C(R$^{10}$)(R$^{11}$))q-, wherein q is 0, 1, 2, 3, 4 or 5;

L is a direct bond or —(C(R$^{10}$)(R$^{11}$))q-; and

Cy is Ar$^1$—B—Ar$^2$, wherein

Ar$^1$ is absent, or an aryl or heteroaryl radical having from 1 to 4 N, O and/or S atoms, which may be unsubstituted or mono-, di- or trisubstituted by halogen, lower alkyl, alkenyl, alkynyl, cycloalkyl, —OR$^{10}$, —NR$^{10}$R$^{11}$, —CN, —COR$^{10}$ or —COOR$^{10}$;

B is a direct bond, —O—, —NR$^{10}$, —SO$_2$, or —(C(R$^{10}$)(R$^{11}$)s-, wherein s is 0, 1, 2, 3, 4 or 5; and Ar$^2$ is aryl or heteroaryl radical having from 1 to 4 N, O and/or S atoms, which may be unsubstituted or mono-, di- or trisubstituted by halogen, lower alkyl, alkenyl, alkynyl, cycloalkyl, —OR$^{10}$, —NR$^{10}$R$^{11}$, —CN, —COR$^{10}$ or —COOR$^{10}$, wherein when Cy is phenyl or biphenyl, $R_1$ is other than —OCH$_3$.

In part, the invention provides a compound of formula II:

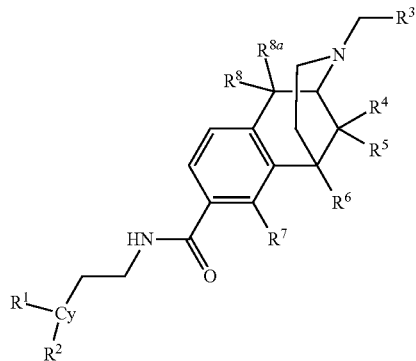

Formula II wherein, Cy, $R^1$, $R^2$, $R^3$, $R^4$, $R^5$, $R^6$, $R^7$, $R^8$, and $R^{8a}$ are as defined above. In some embodiments, $R^1$ is selected from —OH, —CHO, —CONH$_2$—CON(H)CH$_2$CONH$_2$, —CON(H)CH$_2$CH$_2$CONH$_2$, —CON(H)CH$_2$COOH, —CON(H)CH$_2$CH$_2$COOH, —COOH and —COOCH$_3$; or $R^1$ and $R^2$ together with the atoms to which they are attached forms a —OCH$_2$O— fused ring.

In other embodiments, $R^2$ is H, and $R^1$ is selected from —OH, —CHO, —CONH$_2$—CON(H)CH$_2$CONH$_2$, —CON(H)CH$_2$CH$_2$CONH$_2$, —CON(H)CH$_2$COOH, —CON(H)CH$_2$CH$_2$COOH, —COOH and —COOCH$_3$.

In part, the invention provides a compound of formula III, IV, V or VI below:

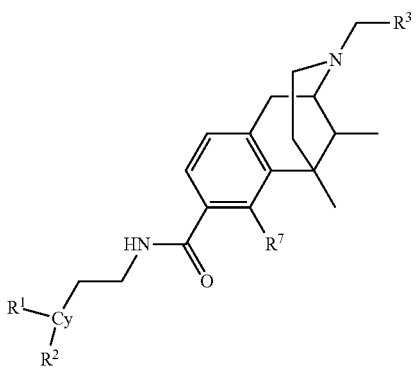

Formula III

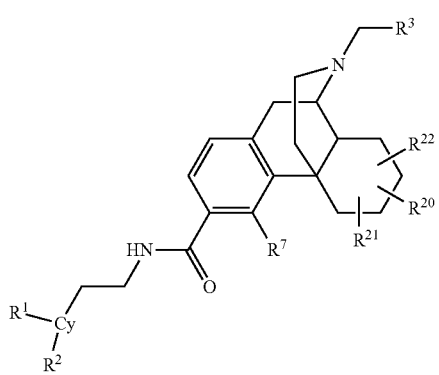

Formula IV

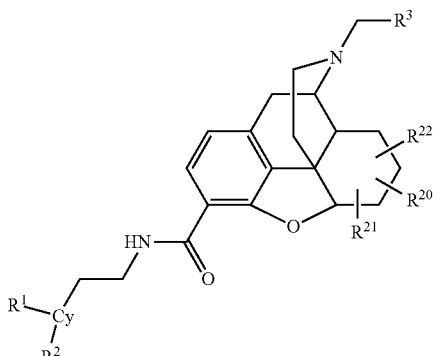

Formula V

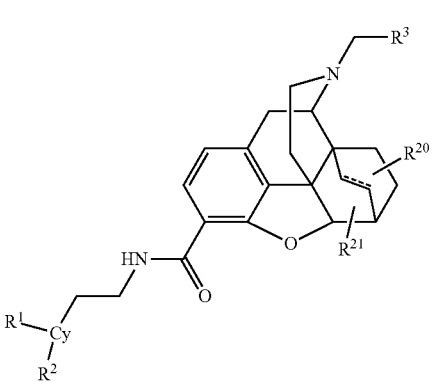

Formula VI wherein, $R^1$, $R^2$, $R^3$, $R^7$ and Cy are as defined above;
each $R^{20}$, $R^{21}$ and $R^{22}$ is chosen from hydrogen, hydroxyl, amino, lower alkoxy, $C_1$-$C_{20}$ alkyl and $C_1$-$C_{20}$ alkyl substituted with hydroxyl or carbonyl; or together, $R^{20}$ and $R^{21}$ together with the carbon to which they are attached, form —CO, or —CS; or together, $R^{20}$ and $R^{21}$, together with the carbon(s) to which they are attached, form a ring. In some embodiments, such a ring is a spiral ring.

In one embodiment, a compound of formula III, IV, V or VI is disclosed wherein $R^1$ is selected from —OH, —CHO, —CONH$_2$—CON(H)CH$_2$CONH$_2$, —CON(H)CH$_2$CH$_2$CONH$_2$, —CON(H)CH$_2$COOH, —CON(H)CH$_2$CH$_2$COOH; or $R^1$ and $R^2$ together with the atoms to which they are attached forms a —OCH$_2$O— fused ring. In another embodiment, $R_2$ is H, and $R^1$ is selected from —OH, —CHO, —CONH$_2$—CON(H)CH$_2$CONH$_2$, —CON(H)CH$_2$CH$_2$CONH$_2$, —CON(H)CH$_2$COOH, —CON(H)CH$_2$CH$_2$COOH.

In part, the invention provides a compound of formula Ia:

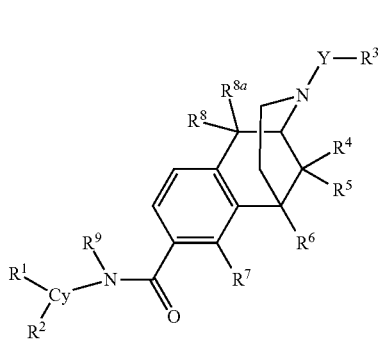

Formula Ia wherein L is a direct bond, and $R^1$, $R^2$, $R^3$, $R^4$, $R^5$, $R^6$, $R^7$, $R^8$, $R^{8a}$, $R^9$ and Cy are as defined above.

R[1] and R[2] can be, independently, small, polar, neutral residues and, in particular, can be selected from the group consisting of substituted or unsubstituted amide groups, including but not limited to carboxamide, thiocarboxamide, acylamine and formamide groups; substituted or unsubstituted amines; substituted or unsubstituted amidines, such as hydroxyamidines; and alkyls substituted by polar neutral residues.

For example, R[1] and R[2] can be, independently, Z, wherein Z is a polar neutral residue, such as $CH_2OR_a$, $CH_2NR_bR_c$, —CN, —$NR_bSO_2$—$R_c$, —C(=W)$R_a$, —$NR_aCOR_b$, —$NR_aCSR_b$, —$SO_2NR_bR_c$, —$NR_b$-$Q_a$-$R_c$, —C(=W)$NR_bR_c$, —C(O)$OR_a$, heterocycle, substituted heterocycle, heteroaryl, and substituted heteroaryl, such as

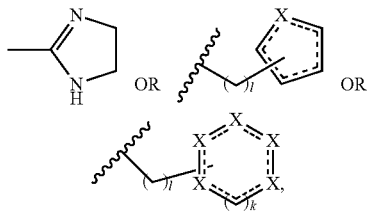

wherein l is 0, 1, 2, 3, 4 or 5; k is 0, 1 or 2; X is C, N, S or O and ----- represents a single or double bond;

$R_a$, $R_b$, $R_c$ are each independently selected from: hydrogen; aryl; substituted aryl; heteroaryl; substituted heteroaryl; heterocyclic or substituted heterocyclic; and substituted or unsubstituted alkyl, alkenyl, alkynyl, cycloalkyl, or cycloalkenyl each containing 0, 1, 2, or 3 or more heteroatoms selected from O, S, or N;

alternatively, $R_a$, $R_b$ and $R_c$ taken together with the attached atom form a heterocyclic or substituted heterocyclic;

$Q_a$ is absent or selected from (C=O), ($SO_2$), (C=NH), (C=S), or (CONR$_a$); and W is O, S, $NOR_a$ or $NR_a$.

In other examples, R[1] and R[2] can be each independently selected from hydrogen, halogen, —OH, —CN, —CHO, —$OCH_3$, —$OCH_2CH_3$, —$OCH(CH_3)_2$, —$NO_2$, —$COR^{10}$, —$COOR^{10}$, —$SO_2R^{10}$, —$CONR^{10}R^{11}$, —$CSNR^{10}R^{11}$, —$CONR^{10}NR^{11}R^{12}$, —$CONR^{10}OR^{11}$, —$CONR^{10}((C(R^{12})(R^{13}))_x CONR^{10}R^{11}$, —$CONR^{10}((C(R^{12})(R^{13}))_x COOR^{11}$, —C(=S)$R^{10}$, —C(=$NOR^{11}$)$R^{10}$, C(=$NR^{10}$)$R^{11}$, —$SO_2NR^{10}R^{11}$, heterocyclyl, optionally substituted lower alkyl, optionally substituted alkenyl, optionally substituted alkynyl, optionally substituted aryl, halo($C_1$-$C_6$)alkyl, halo($C_1$-$C_6$)alkoxy, and ($C_1$-$C_6$)alkylthio.

In other examples, R[1] and R[2], together with the atoms to which they are attached, and a fragment selected from —$OCH_2O$—, or —$OCH_2CH_2O$—, form a ring.

In some embodiments, one of R[1] or R[2] is hydrogen or methyl and the other is —$CONH_2$, —COH, —$CO_2H$, —$CO_2CH_3$, —OH, ($C_1$-$C_6$)alkoxy or CN.

In some embodiments, Cy is selected from:

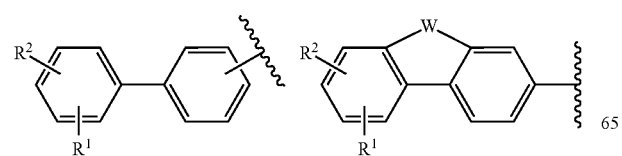

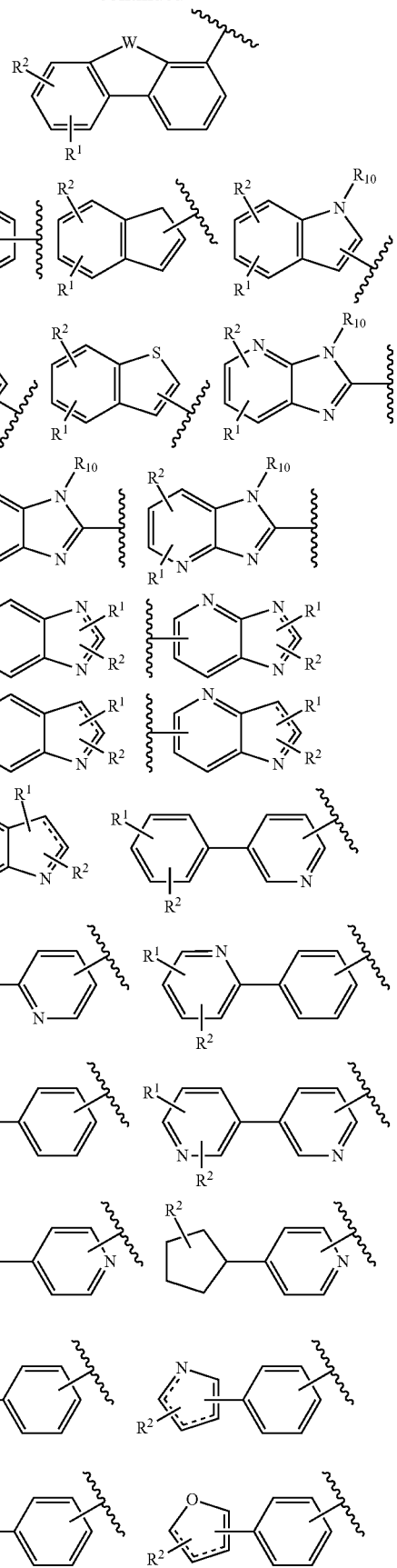

-continued

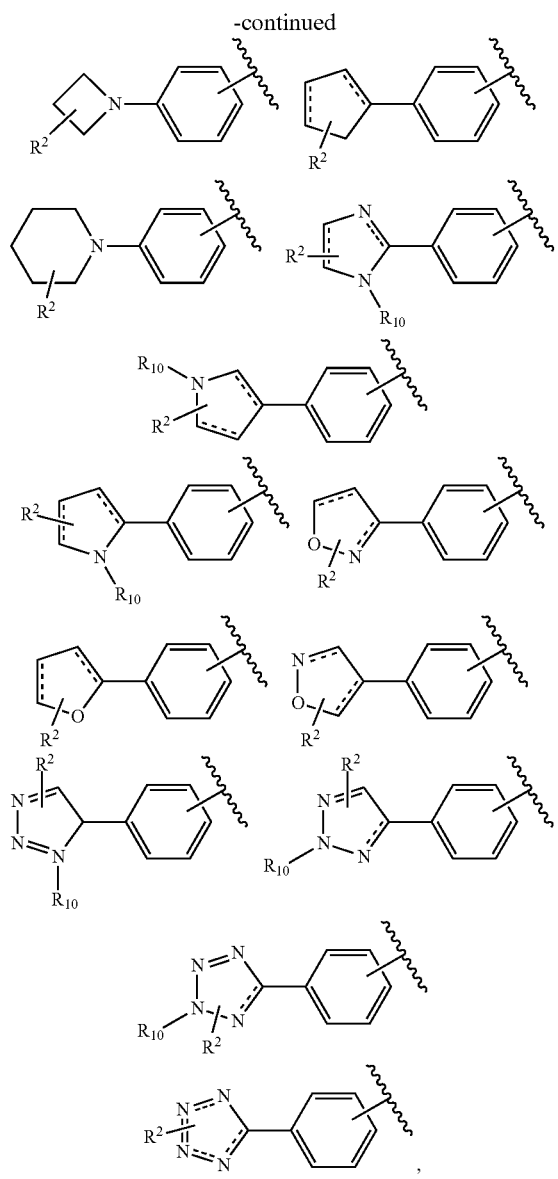

wherein W is selected from $[C(R^9)_2]_n$, $CR^8R^{8a}$, O, $NR^9$, S and $CR^9=CR^9$; and n is 1, 2, 3, 4 or 5.

In some embodiments, $R^3$ is hydrogen. In other embodiments, $R^3$ is heterocyclyl. In still other embodiments, $R^3$ is hydroxyalkyl. In yet other embodiments, $R^3$ is $C_1$-$C_8$ hydrocarbon. In further embodiments, $R^3$ is cyclopropyl or cyclobutyl.

In some embodiments, $R^4$ is hydrogen. In other embodiments, $R^4$ is hydroxyl or amino. In still other embodiments, $R^4$ is lower alkoxy. In yet other embodiments, $R^4$ is $C_1$-$C_{20}$ alkyl or $C_1$-$C_{20}$ alkyl substituted with hydroxyl or carbonyl. In further embodiments, $R^4$ is methyl or ethyl.

In some embodiments, $R^5$ is lower alkyl. In some embodiments, $R^5$ is methyl.

In some embodiments, $R^6$ is lower alkyl. In some embodiments, $R^6$ is methyl.

In some embodiments, $R^7$ is hydrogen. In other embodiments, $R^7$ is $-OR^{10}$. In further embodiments, $R^7$ is hydroxyl. In still other embodiments, $R^7$ is $NR^{10}R^{11}$. In further embodiments, $R^7$ is $NH_2$, $NHCH_3$ or $NH(CH_3)_2$.

In some embodiments, $R^4$, $R^5$, $R^6$ and $R^7$ may form from one, two, three or four rings, said rings having optional additional substitution.

In an embodiment of the invention, $R^8$ and $R^{8a}$ are both hydrogen. In another embodiment, $R^8$ and $R^{8a}$ are taken together to form =O.

In some embodiments, $R^9$ is hydrogen. In other embodiments, $R^9$ is lower alkyl.

In some embodiments, $R^{10}$ and $R^{11}$ are each independently hydrogen. In other embodiments, $R^{10}$ is optionally substituted lower alkoxy and $R^{11}$ is hydrogen or methyl. In still other embodiments, $R^{10}$ is optionally substituted lower alkyl and $R^{11}$ is hydrogen or methyl. In yet other embodiments, $R^{10}$ is optionally substituted aryl and $R^{11}$ is hydrogen or methyl. In yet other embodiments, $R^{10}$ is hydroxyl or amino and $R^{11}$ is hydrogen or methyl. In some embodiments, $R^{10}$ and $R^{11}$, together with the nitrogen atom to which they are attached, form an optionally substituted fused carbocyclic or heterocyclic ring having from 5 to 7 ring members of which up to 3 can be heteroatoms selected from N, O and S. In some embodiments, $R^{10}$ and/or $R^{11}$ is $-NR^{100}R^{101}$.

In these embodiments, $R^{100}$ and $R^{101}$ are each independently selected from hydrogen, optionally substituted lower alkyl, optionally substituted alkenyl, optionally substituted alkynyl, optionally substituted aryl, hydroxyl, and optionally substituted lower alkoxy. In some embodiments, $R^{100}$ and $R^{101}$, together with the nitrogen atom to which they are attached, form an optionally substituted fused carbocyclic or heterocyclic ring having from 5 to 7 ring members of which up to 3 can be heteroatoms selected from N, O and S.

In one aspect of the invention, the compounds described in charts 1-3 are substituted at the phenolic hydroxyl position. For instance, compounds of charts 1-3 are substituted at the phenolic hydroxyl position with $-C(O)N(R_9)LCy(R_1)(R_2)$, wherein the carboxamido moiety replaces the hydroxyl group to give a compound of formula I or formula Ia.

In some embodiments, the compound of formula I or formula Ia is selected from:

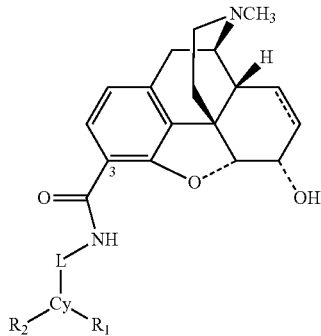

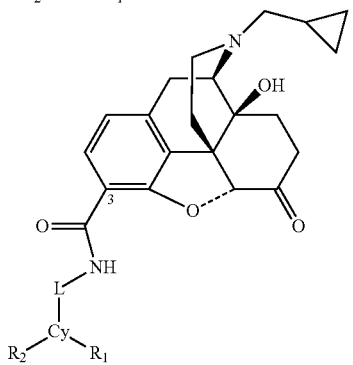

19
-continued
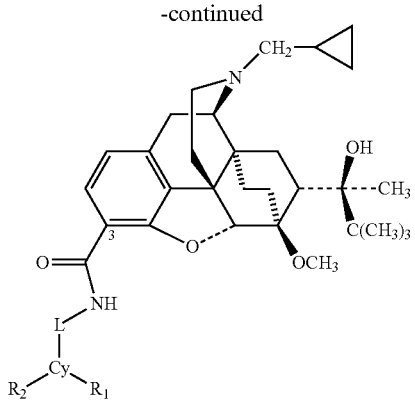
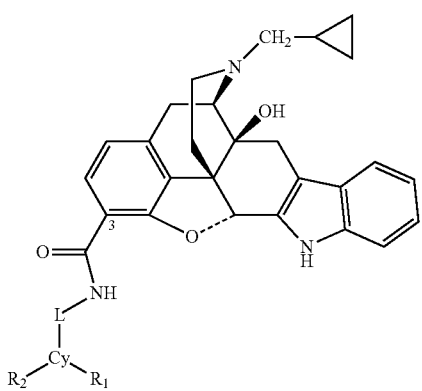
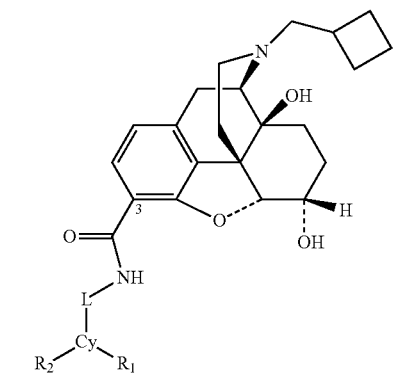
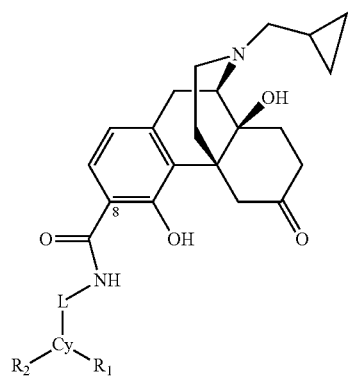
20
-continued
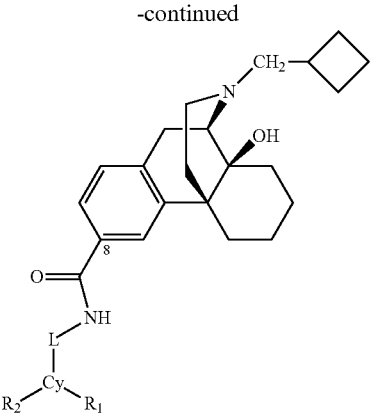
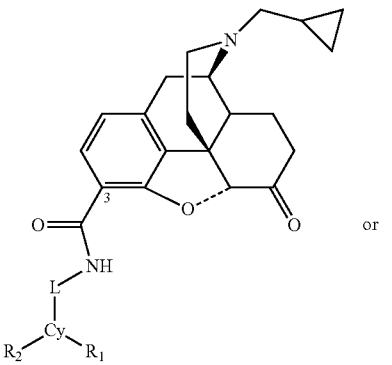
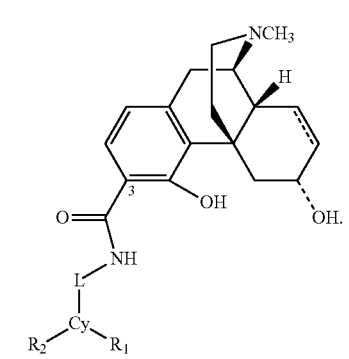
or In some embodiments, the invention provides a compound selected from table 1:
TABLE 1
| No | Structure |
|---|---|
| 1 | 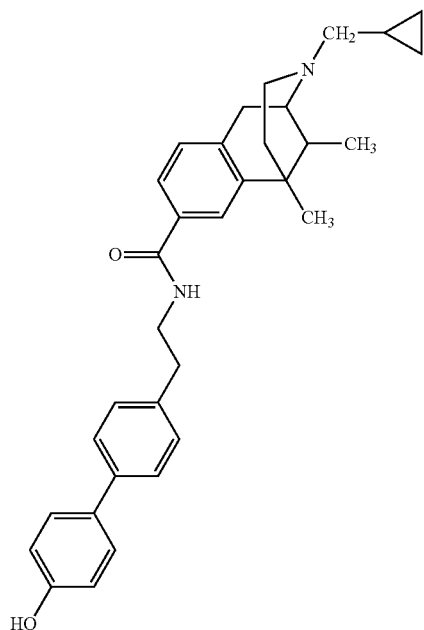 |
| 2 | 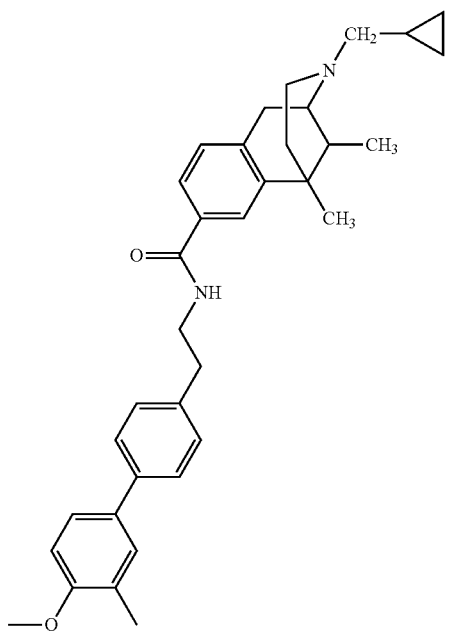 [SMILES: COc1ccc(-c2ccc(CCNC(=O)c3ccc4c(c3)C3(C)CCN(CC5CC5)C(C4)C3C)cc2)cc1C] |
TABLE 1-continued
| No | Structure |
|---|---|
| 3 | 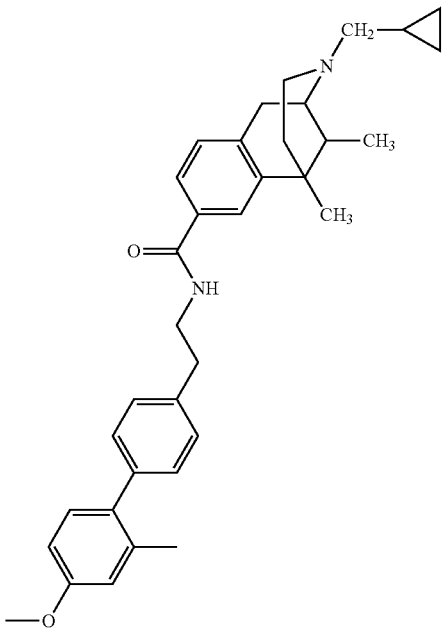 [SMILES: COc1ccc(-c2ccc(CCNC(=O)c3ccc4c(c3)C3(C)CCN(CC5CC5)C(C4)C3C)cc2)c(C)c1] |
| 4 | 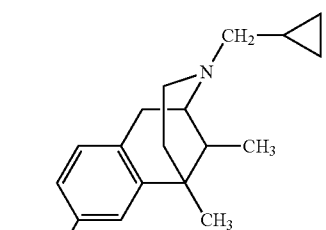 |

TABLE 1-continued
| No | Structure |
|---|---|
| 5 | 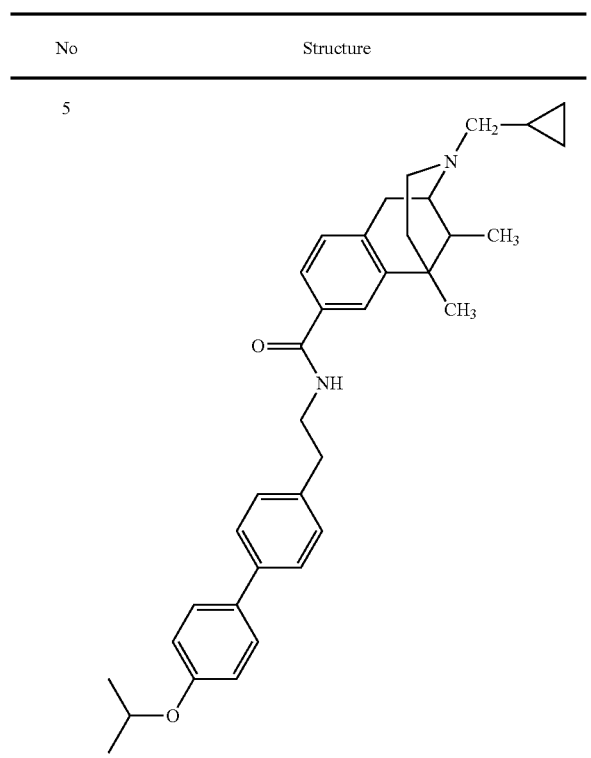 |
| 6 | |
| No | Structure |
|---|---|
| 7 | 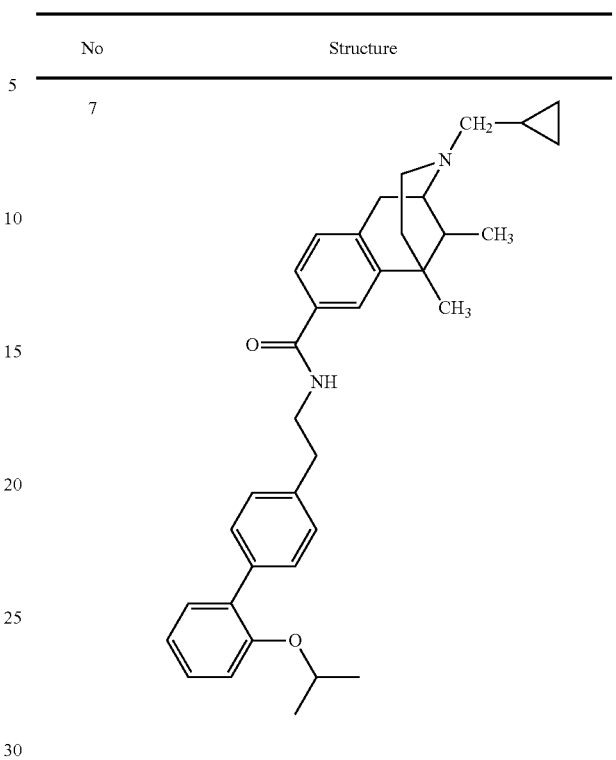 |
| 8 | 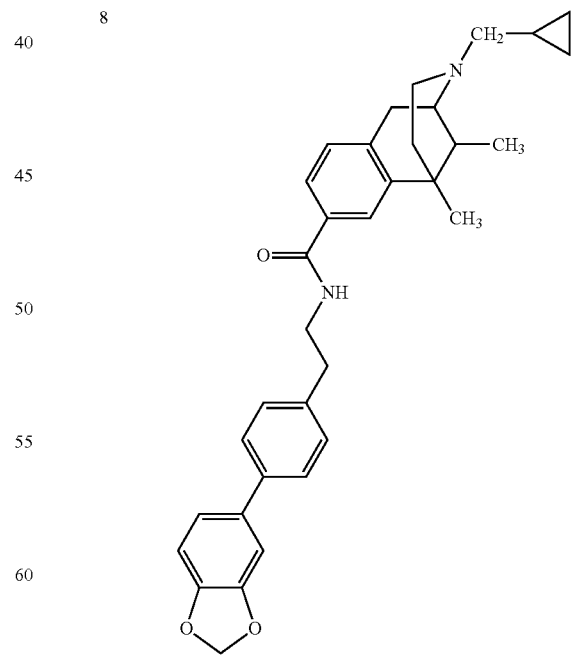 |

TABLE 1-continued

| No | Structure |
|---|---|
| 9 | (structure) |
| 10 | (structure) |
| 11 | (structure) |
| 12 | (structure) |

TABLE 1-continued

| No | Structure |
|---|---|
| 13 | (morphine-derived scaffold with carboxamide linked via ethylene to 4'-hydroxybiphenyl) |
| 14 | (morphinan scaffold with carboxamide linked via ethylene to 4'-hydroxybiphenyl) |
| 15 | (morphine-derived scaffold with carboxamide linked via ethylene to 4'-cyanobiphenyl) |
| 16 | (morphinan scaffold with carboxamide linked via ethylene to 4'-cyanobiphenyl) |

TABLE 1-continued
| No | Structure |
|---|---|
| 17 | 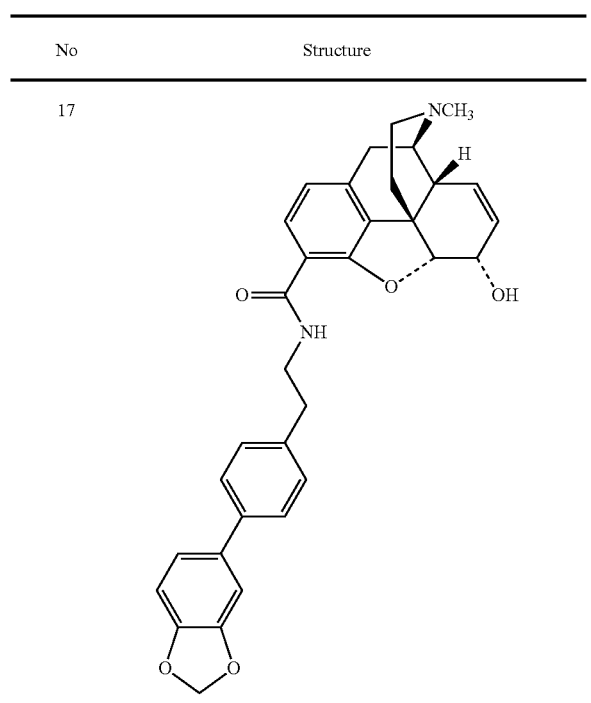 |
| 18 | 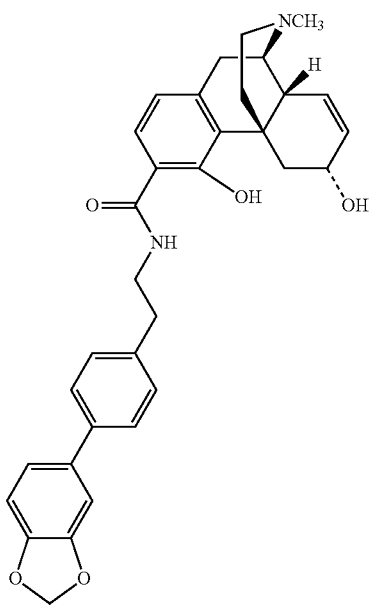 [SMILES: CN1CC[C@]23C[C@@H](O)C=C[C@H]2[C@H]1Cc1ccc(C(=O)NCCc2ccc(-c4ccc5c(c4)OCO5)cc2)c(O)c13] |
TABLE 1-continued
| No | Structure |
|---|---|
| 19 | 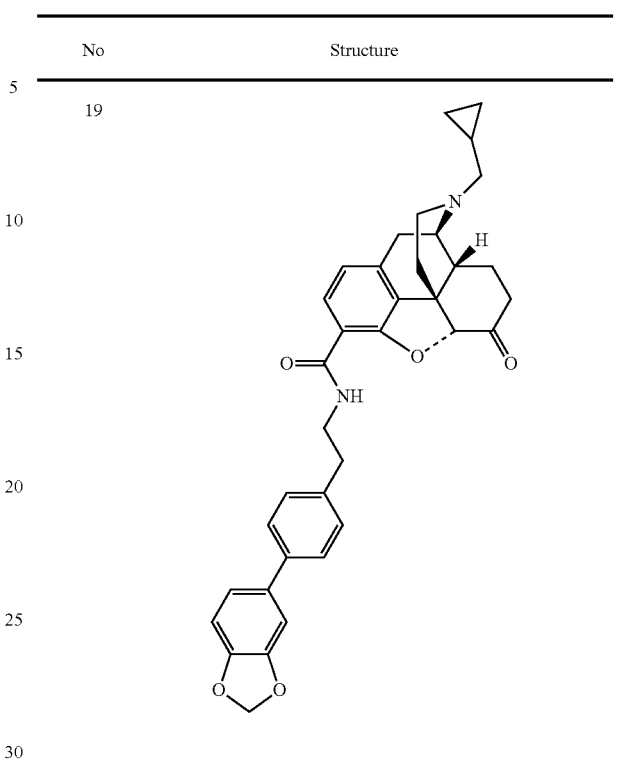 |
| 20 | 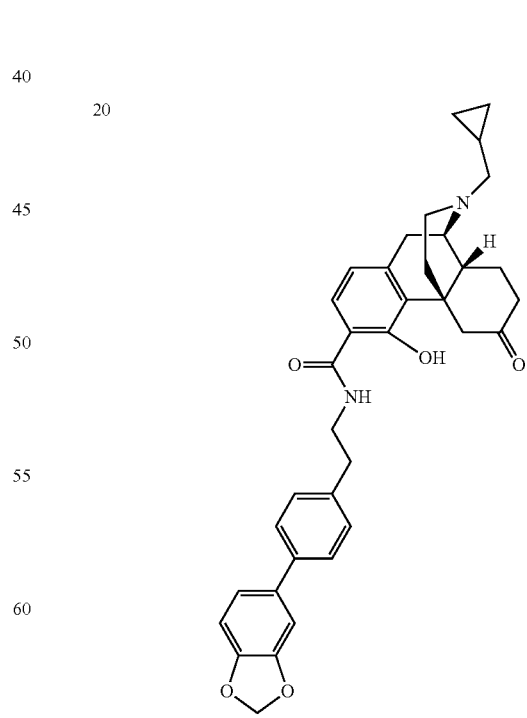 |

TABLE 1-continued
| No | Structure |
|---|---|
| 21 | 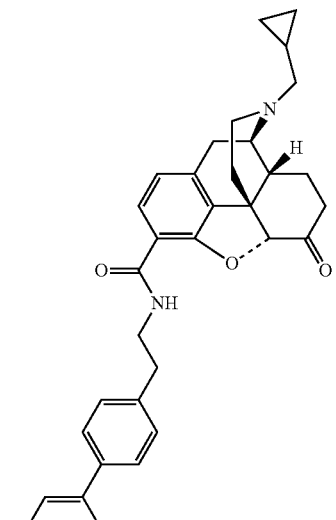 |
| 22 | 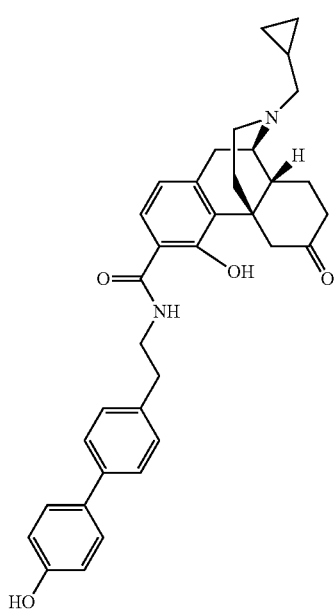 |
TABLE 1-continued
| No | Structure |
|---|---|
| 23 | 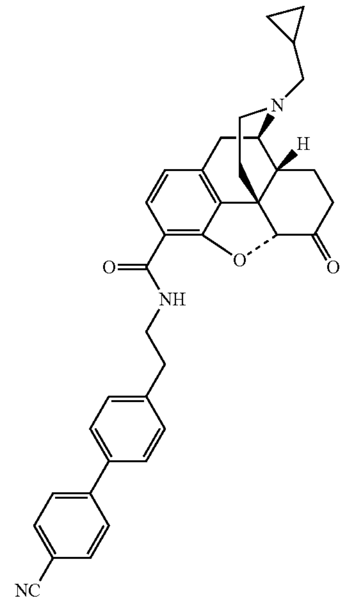 |
| 24 | 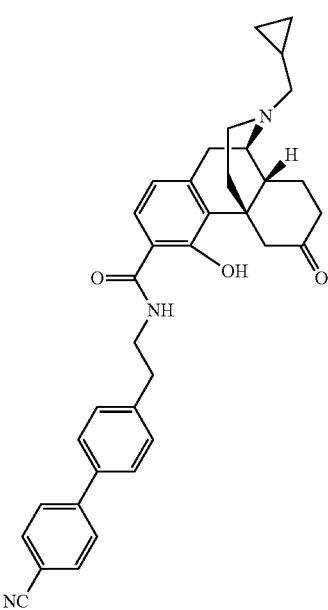 |

TABLE 1-continued

| No | Structure |
|---|---|
| 25 | (structure) |
| 26 | (structure) |
| 27 | (structure) |
| 28 | (structure) |

TABLE 1-continued
| No | Structure |
|----|-----------|
| 29 | 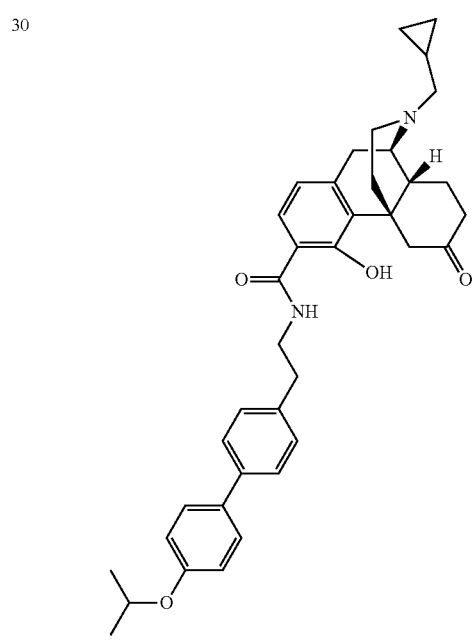 |
| 30 | 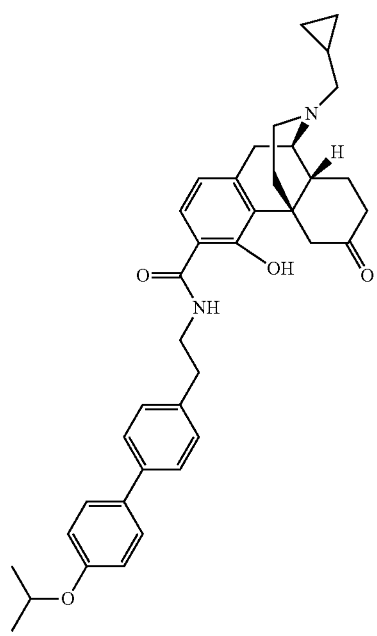 |
TABLE 1-continued
| No | Structure |
|----|-----------|
| 31 | 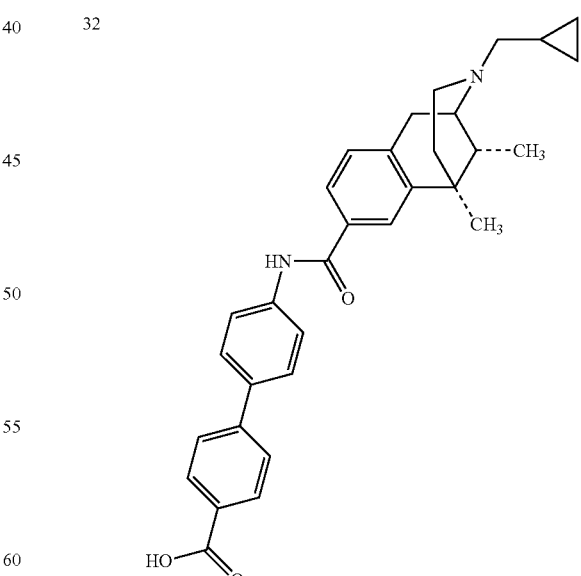 |
| 32 | |

TABLE 1-continued
| No | Structure |
|---|---|
| 33 | 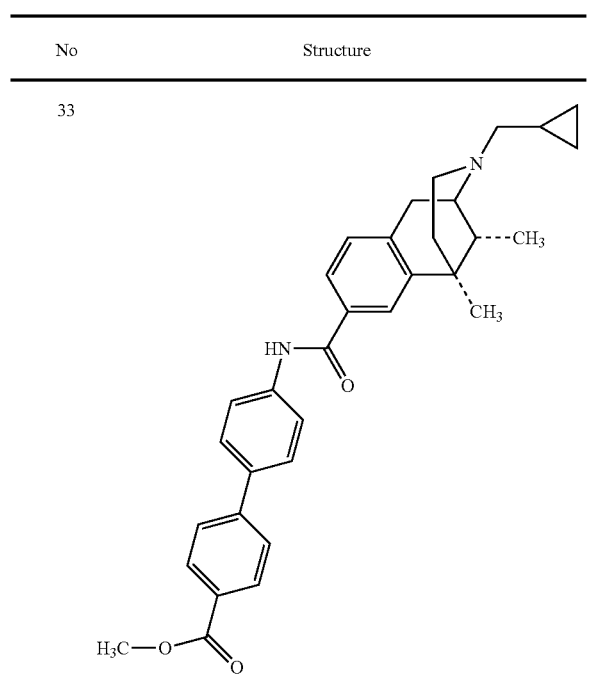 |
| 34 | 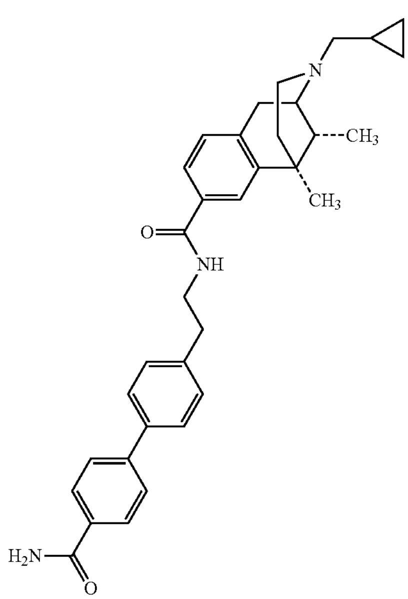 [SMILES: C[C@H]1C2Cc3ccc(C(=O)NCCc4ccc(-c5ccc(C(N)=O)cc5)cc4)cc3[C@@]1(C)CCN2CC1CC1] |
TABLE 1-continued
| No | Structure |
|---|---|
| 35 | 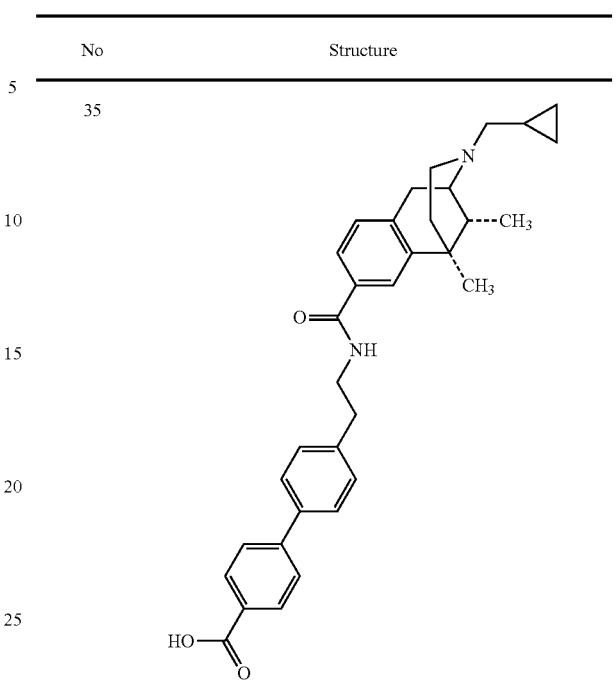 |
| 36 | 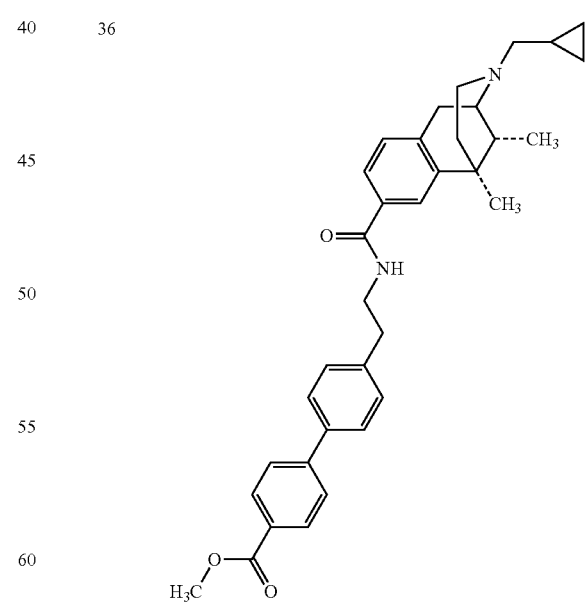 |

TABLE 1-continued
| No | Structure |
|---|---|
| 37 | 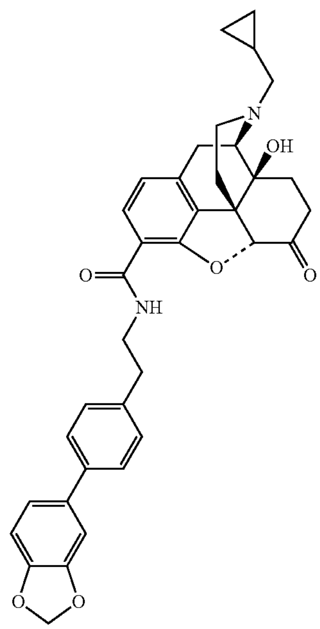 |
| 38 | 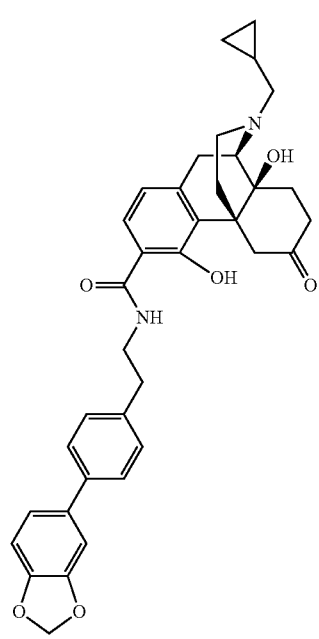 [SMILES: O=C1CC[C@@]2(O)[C@H]3Cc4ccc(C(=O)NCCc5ccc(-c6ccc7c(c6)OCO7)cc5)c(O)c4[C@@]2(CCN3CC2CC2)C1] |
| 39 | |
| 40 | 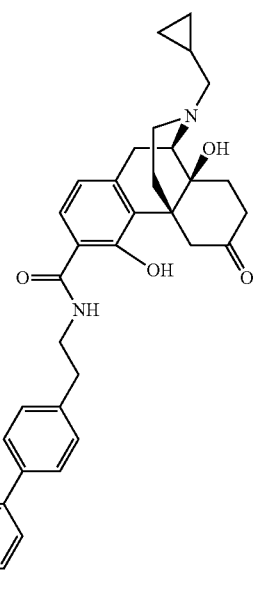 |

TABLE 1-continued
| No | Structure |
|---|---|
| 41 | 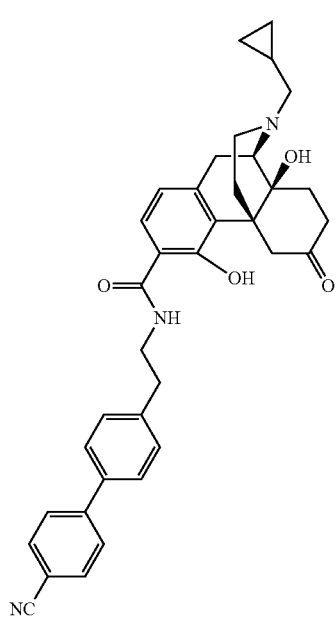 |
| 42 | 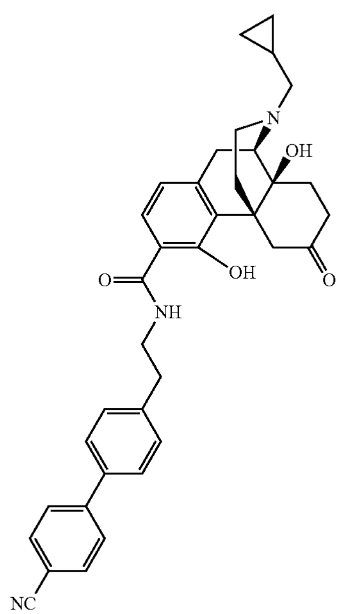 [SMILES: O=C1CC[C@@]2(O)[C@H]3Cc4ccc(C(=O)NCCc5ccc(-c6ccc(O)cc6)cc5)c(O)c4[C@@]2(CCN3CC2CC2)C1] |
TABLE 1-continued
| No | Structure |
|---|---|
| 43 | 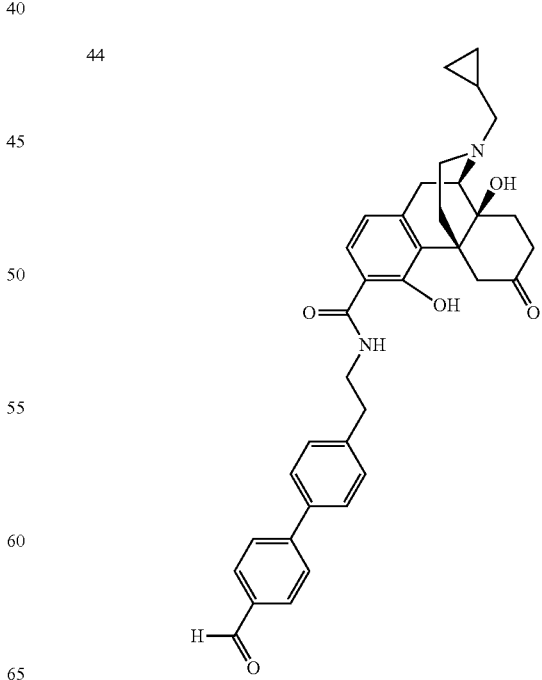 |
| 44 | 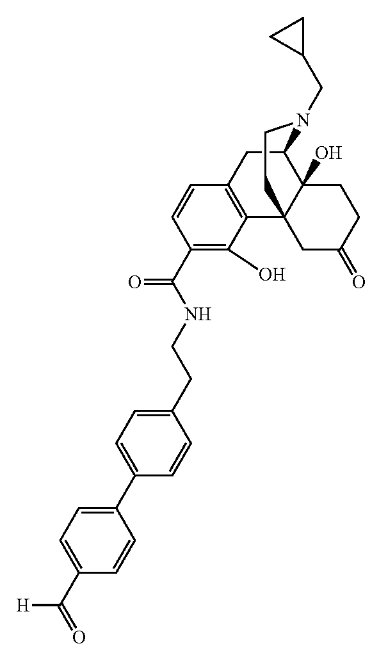 [SMILES: O=Cc1ccc(-c2ccc(CCNC(=O)c3ccc4c(c3O)[C@]35CCN(CC6CC6)[C@H](C4)[C@]3(O)CCC(=O)C5)cc2)cc1] |

TABLE 1-continued
| No | Structure |
|---|---|
| 45 | 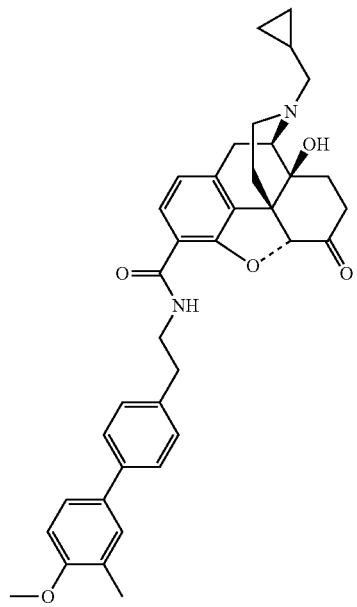 |
| 46 | 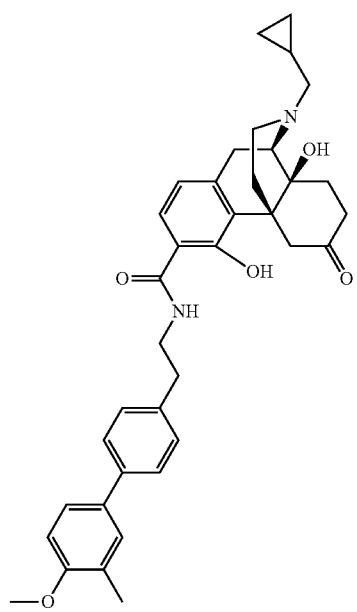 |
| 47 | 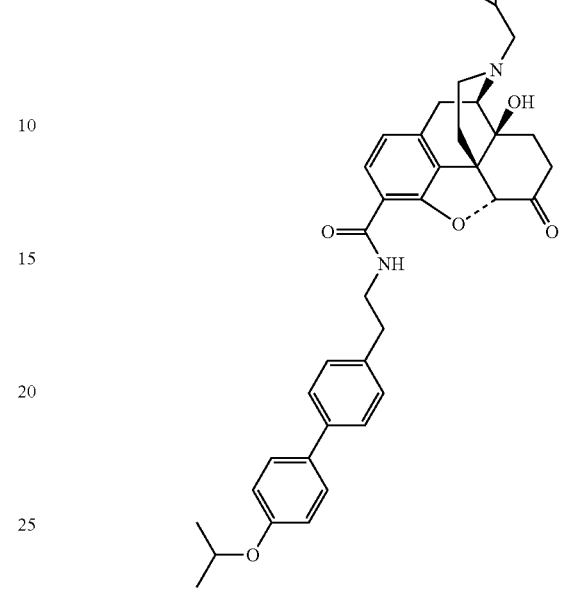 |
| 48 | 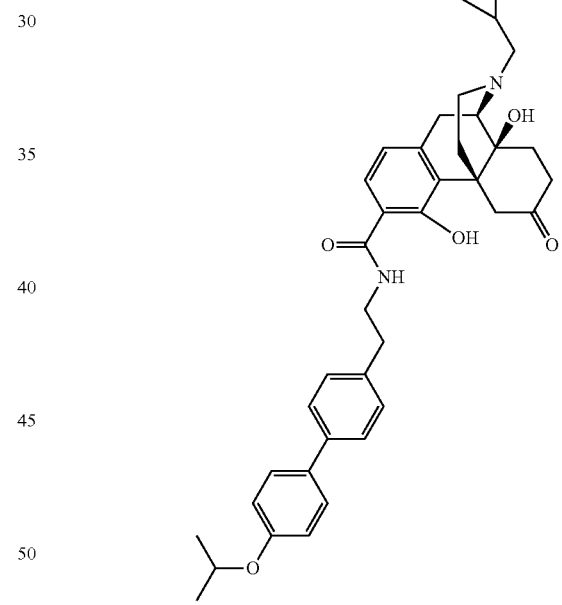 |
In some embodiments of the invention, Cy-R$^1$R$^2$ is of formula
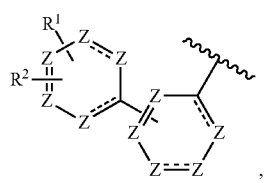
wherein Z is CR$^{10}$ (with R$^{10}$ defined as above) or N. In these instances, Z must be C at the point of attachment of the distal ring to the proximal ring. Additionally, at the points of attachment of $R^1$ and $R^2$, Z will be $CR^1$ and $CR^2$, respectively. In some embodiments, Cy-$R^1R^2$ will have the structure:

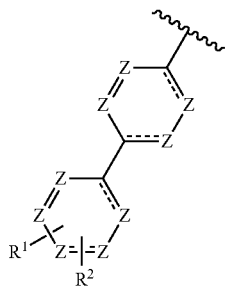

In some of these embodiments, one of $R^1$ and $R^2$ is in the para position relative to B (the point of attachment of the distal ring to the proximal ring) and the other of $R^1$ and $R^2$ is hydrogen.

In some embodiments of the invention, $Ar^2$ is phenyl and one of $R^1$ or $R^2$ is in the para position relative to B.

In some embodiments of the invention, Cy-$R^1R^2$ has the structure:

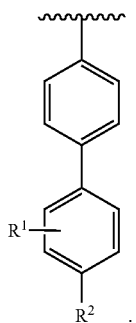

The phenolic hydroxyls of benzomorphans and morphinans can be chemically converted to carboxamides by a simple, flexible and convenient route described in U.S. Pat. Nos. 6,784,187, 7,057,035, US 20070021457, and WO 2010/011619.

It is known in the art that compounds that are μ, δ and κ agonists exhibit analgesic activity; compounds that are selective μagonists exhibit anti-diarrheal activity and are useful in treating dyskinesia; μ antagonists and κ agonists are useful in treating heroin, cocaine, alcohol and nicotine addiction; κ agonists are also anti-pruritic agents and are useful in treating hyperalgesia. Recently it has been found [Peterson et al. Biochem. Pharmacol. 61, 1141-1151 (2001)] that κ agonists are also useful in treating retroviral infections. In general, the dextrorotatory isomers of morphinans of type III above are useful as antitussives and anticonvulsants. Opiate binding is also related to the treatment of arthritis. (Keates et al., Anesth Analg 1999; 89:409-15). Furthermore it has been reported that in patients suffering from osteoarthritis, μ- and δ-opioid receptors are synthesized and located in synovial lining cells, lymphocytes, and macrophages surrounding the vessels in synovial tissues, and may play a role in the regulation and modulation of inflammation. (Tanaka et al., Modern Rheumatology, 2003, 13(4) 326-332).

Opioid receptor ligands having known high affinity are shown in charts 1-3. Replacement of the phenolic OH with the —C(O)N($R_9$)LCy($R_1$)($R_2$) residue in these compounds produces compounds that exhibit similar activity and better bioavailability.

Binding assays used to screen compounds are similar to those previously reported by Neumeyer et al., Design and Synthesis of Novel Dimeric Morphinan Ligands for κ and μ Opioid Receptors. J. Med. Chem. 2003, 46, 5162. Membrane protein from CHO cells that stably expressed one type of the human opioid receptor were incubated with 12 different concentrations of the compound in the presence of either 1 nM [$^3$H]U69,593[10] (κ), 0.25 nM [$^3$H]DAMGO[11] (μ) or 0.2 nM [$^3$H]naltrindole[12] (δ) in a final volume of 1 mL of 50 mM Tris-HCl, pH 7.5 at 25° C. Incubation times of 60 min were used for [$^3$H]U69,593 and [$^3$H]DAMGO. Because of a slower association of [$^3$H]naltrindole with the receptor, a 3 h incubation was used with this radioligand. Samples incubated with [$^3$H]naltrindole also contained 10 mM $MgCl_2$ and 0.5 mM phenylmethylsulfonyl fluoride. Nonspecific binding was measured by inclusion of 10 μM naloxone. The binding was terminated by filtering the samples through Schleicher & Schuell No. 32 glass fiber filters using a Brandel 48-well cell harvester. The filters were subsequently washed three times with 3 mL of cold 50 mM Tris-HCl, pH 7.5, and were counted in 2 mL Ecoscint A scintillation fluid. For [$^3$H]naltrindole and [$^3$H]U69,593 binding, the filters were soaked in 0.1% polyethylenimine for at least 60 min before use. $IC_{50}$ values were calculated by least squares fit to a logarithm-probit analysis. $K_i$ values of unlabeled compounds were calculated from the equation $K_i=(IC_{50})/1+S$ where S=(concentration of radioligand)/($K_d$ of radioligand).[13] Data are the mean±SEM from at least three experiments performed in triplicate.

[$^{35}$S]GTPγS Binding Assays. In a final volume of 0.5 mL, 12 different concentrations of each test compound were incubated with 15 μg (κ), 10 μg (δ) or 7.5 μg (μ) of CHO cell membranes that stably expressed either the human κ, δ or μ opioid receptor. The assay buffer consisted of 50 mM Tris-HCl, pH 7.4, 3 mM $MgCl_2$, 0.2 mM EGTA, 3 μM GDP, and 100 mM NaCl. The final concentration of [$^{35}$S]GTPγS was 0.080 nM. Nonspecific binding was measured by inclusion of 10 μM GTPγS. Binding was initiated by the addition of the membranes. After an incubation of 60 min at 30° C., the samples were filtered through Schleicher & Schuell No. 32 glass fiber filters. The filters were washed three times with cold 50 mM Tris-HCl, pH 7.5, and were counted in 2 mL of Ecoscint scintillation fluid. Data are the mean $E_{max}$ and $EC_{50}$ values ±S.E.M. from at least three separate experiments, performed in triplicate. For calculation of the $E_{max}$ values, the basal [$^{35}$S]GTPγS binding was set at 0%. To determine antagonist activity of a compound at the μ opioid receptors, CHO membranes expressing the μ opioid receptor, were incubated with 12 different concentrations of the compound in the presence of 200 nM of the μ agonist DAMGO. To determine antagonist activity of a compound at the κ opioid receptors, CHO membranes expressing the κ opioid receptor, were incubated with the compound in the presence of 100 nM of the κ agonist U50,488. To determine if a compound was an antagonist at δ receptors, CHO membranes expressing the δ receptor were incubated with 12 different concentrations of the test compound in the presence of 10 nM of the δ-selective agonist SNC 80.

EXAMPLES

Cyclazocine Subseries

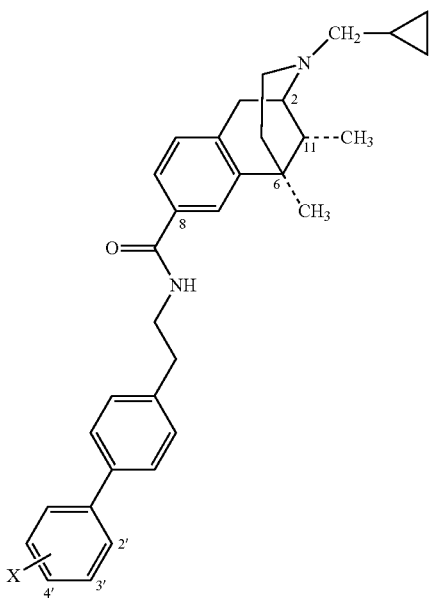

$K_i$(nM ±S.E.)

| Compound No. | | X | [$^3$H]DAMGO (μ) | [$^3$H]Naltrindole (δ) | [$^3$H]U69,593 (κ) |
|---|---|---|---|---|---|
| Reference | (±) | H | 0.30 ± 0.02 | 0.74 ± 0.019 | 1.8 ± 0.19 |
| Reference | (−) | H | 0.25 ± 0.031 | 0.24 ± 0.014 | 0.35 ± 0.009 |
| Reference | (+) | H | 6.4 ± 0.50 | 9.9 ± 0.44 | 8.5 ± 1.07 |
| 1 | (±) | 4'-OH | 0.0056 ± 0.00073 | 0.81 ± 0.12 | 0.49 ± 0.011 |
| 1A | (−) | 4'-OH | 0.0049 ± 0.001 | 0.78 ± 0.05 | 0.36 ± 0.018 |
| 2 | (±) | 3'-CH$_3$-4'-OCH$_3$ | 0.059 ± 0.0050 | 1.5 ± 0.14 | 1.7 ± 0.14 |
| 3 | (±) | 2'CH$_3$-4'-OCH$_3$ | 0.23 ± 0.0056 | 1.1 ± 0.18 | 1.3 ± 0.11 |
| 4 | (±) | 4'-OCH$_2$CH$_3$ | 0.64 ± 0.058 | 3.4 ± .039 | 3.3 ± 0.32 |
| 5 | (±) | 4'-OCH(CH$_3$)$_2$ | 0.23 ± 0.041 | 1.9 ± 0.21 | 1.6 ± 0.11 |
| 6 | (±) | 3'-OCH(CH$_3$)$_2$ | 0.43 ± 0.041 | 3.9 ± 1.4 | 2.4 ± 0.25 |
| 7 | (±) | 2'-OCH(CH$_3$)$_2$ | 0.12 ± 0.0018 | 0.55 ± 0.025 | 1.8 ± 0.17 |
| 8 | (±) | 3',4'-OCH$_2$O— | 0.0016 ± 0.0034 | 1.0 ± 0.12 | 0.73 ± 0.049 |
| 9 | (±) | 4'-CN | 0.017 ± 0.00075 | 3.0 ± 0.11 | 1.0 ± 0.095 |
| 10 | (±) | 4'-CHO | 0.0020 ± 0.00029 | 2.5 ± 0.12 | 1.8 ± 0.038 |
| 34 | (±) | 4'-CONH$_2$ | 0.0052 ± 0.00055 | 1.0 ± 0.018 | 0.91 ± 0.066 |
| 35 | (±) | 4'-CO$_2$H | 2.3 ± 0.16 | 68 ± 9.0 | 55 ± 4.1 |
| 36 | (±) | 4'-CO$_2$CH$_3$ | 0.0091 ± 0.00071 | 1.5 ± 0.062 | 1.1 ± 0.13 |

Antinociceptive activity is evaluated by the method described in Jiang et al. [*J. Pharmacol. Exp. Ther.* 264, 1021-1027 (1993), page 1022]. The ED$_{50}$'s of compounds of the invention are expected to be under 100 nmol in the mouse acetic acid writhing test when administered i.c.v., and an increase in the duration of action is expected for compounds of the invention compared to their "parents" when given by i.p. administration.

Definitions

Throughout this specification the terms and substituents retain their definitions.

Alkyl is intended to include linear, branched, or cyclic hydrocarbon structures and combinations thereof. A combination would be, for example, cyclopropylmethyl. Lower alkyl refers to alkyl groups of from 1 to 6 carbon atoms. Examples of lower alkyl groups include methyl, ethyl, propyl, isopropyl, cyclopropyl, butyl, s- and t-butyl, cyclobutyl and the like. Preferred alkyl groups are those of C$_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, nor-bornyl and the like.

Alkoxy or alkoxyl refers to groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

Arylalkyl means an alkyl residue attached to an aryl ring. Examples are benzyl, phenethyl and the like. Heteroarylalkyl means an alkyl residue attached to a heteroaryl ring. Examples include, e.g., pyridinylmethyl, pyrimidinylethyl and the like.

C$_1$ to C$_{20}$ hydrocarbon means a linear, branched, or cyclic residue comprised of hydrogen and carbon as the only elemental constituents and includes alkyl, cycloalkyl, polycycloalkyl, alkenyl, alkynyl, aryl and combinations thereof. Examples include, e.g., benzyl, phenethyl, cyclohexylmethyl, camphoryl and naphthylethyl.

The term "halogen" means fluorine, chlorine, bromine or iodine. In one embodiment, halogen may be fluorine or chlorine.

The terms "haloalkyl" and "haloalkoxy" mean alkyl or alkoxy, respectively, substituted with one or more halogen atoms.

Heterocycle means a cycloalkyl or aryl residue in which one to four of the carbons is replaced by a heteroatom such as oxygen, nitrogen or sulfur. Heteroaryls form a subset of heterocycles. Examples of heterocycles that fall within the scope of the invention include, e.g., pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, alkyl, acyl, alkoxyalkyl, hydroxyloweralkyl, phenyl, heteroaryl, benzenesulfonyl, hydroxy, loweralkoxy, haloalkoxy, carboxy, carboalkoxy (also referred to as alkoxycarbonyl), alkoxycarbonylamino, carboxamido (also referred to as alkylaminocarbonyl), cyano, carbonyl, acetoxy, nitro, amino, alkylamino, dialkylamino, mercapto, alkylthio, sulfoxide, sulfone, sulfonylamino, acylamino, amidino, aryl, benzyl, heterocyclyl, phenoxy, benzyloxy, heteroaryloxy, hydroxyimino, alkoxyimino, oxaalkyl, aminosulfonyl, trityl, amidino, guanidino, ureido, and benzyloxy.

Virtually all of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as their racemic and optically pure forms. In general it has been found that the levo isomer of morphinans and benzomorphans is the more potent antinociceptive agent, while the dextro isomer may be useful as an antitussive or antispasmodic agent. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

Some of the compounds of the invention are quaternary salts, i.e. cationic species. Therefore they will always be presented as salts, and the term "pharmaceutically acceptable salt" refers to salts whose counter ion (anion) derives from pharmaceutically acceptable non-toxic acids including inorganic acids, organic acids and water (which formally furnishes the hydroxide anion). Suitable pharmaceutically acceptable anions for the compounds of the present invention include hydroxide, acetate, benzenesulfonate (besylate), benzoate, bicarbonate, bisulfate, carbonate, camphorsulfonate, citrate, ethanesulfonate, fumarate, gluconate, glutamate, glycolate, bromide, chloride, isethionate, lactate, maleate, malate, mandelate, methanesulfonate, mucate, nitrate, pamoate, pantothenate, phosphate, succinate, sulfate, tartrate, trifluoroacetate, p-toluenesulfonate, acetamidobenzoate, adipate, alginate, aminosalicylate, anhydromethylenecitrate, ascorbate, aspartate, calcium edetate, camphorate, camsylate, caprate, caproate, caprylate, cinnamate, cyclamate, dichloroacetate, edetate (EDTA), edisylate, embonate, estolate, esylate, fluoride, formate, gentisate, gluceptate, glucuronate, glycerophosphate, glycolate, glycollylarsanilate, hexylresorcinate, hippurate, hydroxynaphthoate, iodide, lactobionate, malonate, mesylate, napadisylate, napsylate, nicotinate, oleate, orotate, oxalate, oxoglutarate, palmitate, pectinate, pectinate polymer, phenylethylbarbiturate, picrate, pidolate, propionate, rhodanide, salicylate, sebacate, stearate, tannate, theoclate, tosylate and the like. The desired salt may be obtained by ion exchange of whatever counter ion is obtained in the synthesis of the quat. These methods are well known to persons of skill. Although pharmaceutically acceptable counter ions will be preferred for preparing pharmaceutical formulations, other anions are quite acceptable as synthetic intermediates. Thus X may be pharmaceutically undesirable anions, such as iodide, oxalate, trifluoromethanesulfonate and the like, when such salts are chemical intermediates. When the compounds of the invention are bisquats, one may employ as counter ions either two monoanionic species (e.g. $Cl_2$) or a single dianionic species (e.g. fumarate). Similarly, one could employ oligoanionic species and make salts having appropriate ratios of quat to counterion, such as (quat)$_3$ citrates. These would be obvious equivalents. In some embodiments, the nitrogen of the morphinan or benzomorphan core structure is quaternized. Quaternization can be achieved by methylation of a tertiary nitrogen atom.

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated. It may be found upon examination that certain members of the claimed genus are not patentable to the inventors in this application. In this event, subsequent exclusions of species from the compass of applicants' claims are to be considered artifacts of patent prosecution and not reflective of the inventors' concept or description of their invention; the invention encompasses all of the members of the genus (I) that are not already in the possession of the public.

Abbreviations

The following abbreviations and terms have the indicated meanings throughout:

------ represents a single or double bond;
Ac=acetyl
BNB=4-bromomethyl-3-nitrobenzoic acid
Boc=t-butyloxy carbonyl
BPE=2(4-biphenylyl)ethyl=

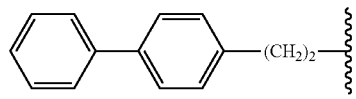

Bu=butyl
c-=cyclo
DAMGO=Tyr-ala-Gly-NMePhe-NHCH$_2$OH
DBU=diazabicyclo[5.4.0]undec-7-ene
DCM=dichloromethane=methylene chloride=CH$_2$Cl$_2$
DEAD=diethyl azodicarboxylate
DIC=diisopropylcarbodiimide
DIEA=N,N-diisopropylethyl amine
DMAP=4-N,N-dimethylaminopyridine
DMF=N,N-dimethylformamide
DMSO=dimethyl sulfoxide
DOR=delta opioid receptor
DPPF=1,1'-bis(diphenylphosphino)ferrocene
DVB=1,4-divinylbenzene
EEDQ=2-ethoxy-1-ethoxycarbonyl-1,2-dihydroquinoline
Fmoc=9-fluorenylmethoxycarbonyl
GC=gas chromatography
HATU=O-(7-Azabenzotriazol-1-yl)-1,1,3,3-tetramethyluronium hexafluorophosphate
HOAc=acetic acid
HOBt=hydroxybenzotriazole
KOR=kappa opioid receptor Me=methyl
mesyl=methanesulfonyl
MOR=mu opioid receptor
MTBE=methyl t-butyl ether
NMO=N-methylmorpholine oxide
PEG=polyethylene glycol
Ph=phenyl
PhOH=phenol
NP=pentafluorophenol
PPTS=pyridinium p-toluenesulfonate
PyBroP=bromo-tris-pyrrolidino-phosphonium hexafluorophosphate
rt=room temperature
sat'd=saturated
s-=secondary
t-=tertiary
TBDMS=t-butyldimethylsilyl
TFA=trifluoroacetic acid
THF=tetrahydrofuran
TMOF=trimethyl orthoformate
TMS=trimethylsilyl
tosyl=p-toluenesulfonyl
Trt=triphenylmethyl
U69,593=

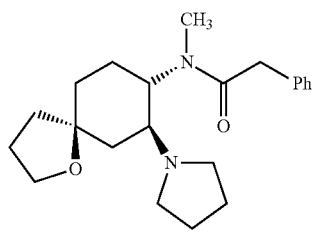

It may happen that residues in the substrate of interest require protection and deprotection during the conversion of the phenol hydroxyl. Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is below, the person of ordinary skill can readily envision those groups that would be suitable as "protecting groups". Suitable groups for that purpose are discussed in standard textbooks in the field of chemistry, such as *Protective Groups in Organic Synthesis* by T. W. Greene [John Wiley & Sons, New York, 1991], which is incorporated herein by reference.

The compounds of the invention are synthesized by one of the routes described below:

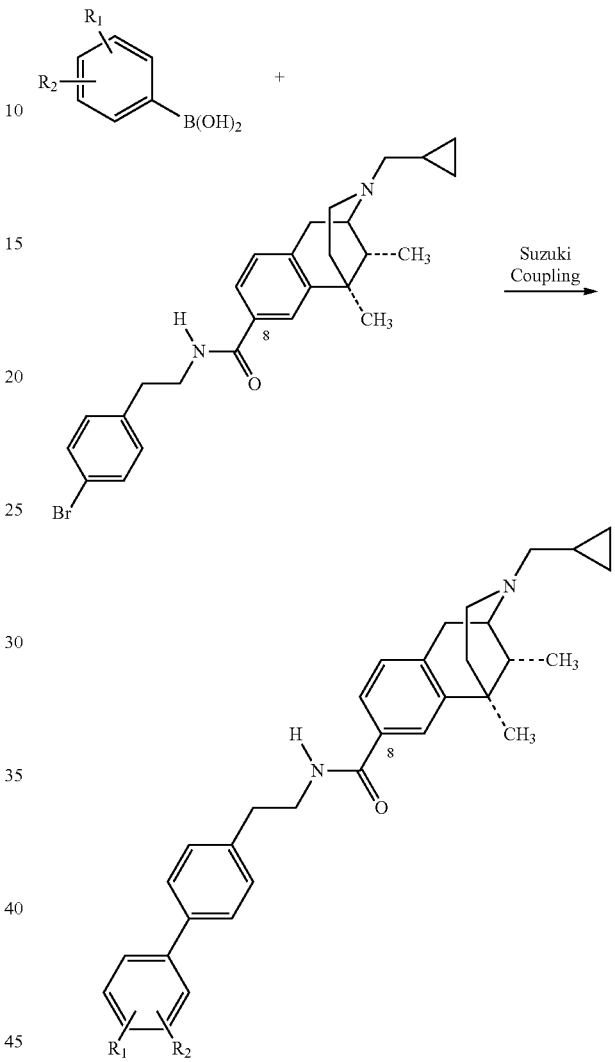

In general, the method of replacing a phenolic —OH with triflate, is described in U.S. Pat. No. 6,784,187, the contents of which are incorporated herein by reference.

Proton NMR spectra and in certain cases $^{13}$C NMR were obtained on a Varian Unity-300 or 500 NMR spectrometer with tetramethylsilane as an internal reference for samples dissolved in $CDCl_3$. Samples dissolved in $CD_3OD$ and DMSO-$d_6$ were referenced to the solvent. Proton NMR multiplicity data are denoted by s (singlet), d (doublet), t (triplet), q (quartet), m (multiplet), dd (doublet of doublets), and br (broad). Coupling constants are in hertz. Direct insertion probe chemical ionization mass spectral data were obtained on a Shimadzu GC-17A GC-MS mass spectrometer. Direct infusion electrospray ionization (in positively charged ion mode) mass spectral data were obtained on an Agilent 1100 series LC/MSD system (Germany). Melting points were determined on a Meltemp capillary melting point apparatus and were uncorrected. Infrared spectral data were obtained on a Perkin-Elmer Paragon 1000 FT-IR spectrophotometer. Optical rotation data was obtained from a Perkin-Elmer 241 polarimeter. The assigned structure of all test compounds and intermediates were consistent with the data. Carbon, hydrogen, and nitrogen elemental analyses for all novel targets were performed by Quantitative Technologies Inc., Whitehouse, N.J., and were within ±0.4% of theoretical values except as noted; the presence of water or other solvents was confirmed by proton NMR. Reactions were generally performed in an argon or nitrogen atmosphere. Commercially purchased chemicals were used without purification unless otherwise noted. The following reagents were purchased from Aldrich Chemical Company: N-hydroxysuccinimide, phenethylamine, 3-phenyl-1-propylamine, 4-aminobiphenyl, palladium acetate, 4-phenylbenzylamine and benzyl amine. The following reagent was purchased from Trans World Chemicals: 2-(4-biphenyl ethylamine). The following reagents were purchased from Strem Chemicals, Incorporated: 1,1'-bis(diphenyl-phosphino)ferrocene (dppf) and dichloro[1,1'-bis(diphenylphosphino)-ferrocene]palladium (II) dichloromethane adduct [PdCl$_2$(dppf)]. Pyridine was distilled from KOH. DMF and DMSO were distilled over CaH$_2$ under reduced pressure. Silica gel (Bodman Industries, ICN SiliTech 2-63 D 60A, 230-400 Mesh) was used for all flash chromatography. Amines were purchased from Aldrich Chemical Company and used as received unless otherwise indicated. Toluene and Et$_2$O were distilled from sodium metal. THF was distilled from sodium/benzophenone ketyl. Pyridine was distilled from KOH. Methylene chloride was distilled from CaH$_2$. DMF and DMSO were distilled from CaH$_2$ under reduced pressure. Methanol was dried over 3±molecular sieves prior to use. Silica gel (Bodman Industries, ICN SiliTech 2-63 D 60A, 230-400 Mesh) was used for flash column chromatography.

In general, the chemistry described above works in the presence of the variety of functional groups found on known core structures. The exceptions would be morphine and congeners having a free 6-OH, which can be protected by a TBDPS (t-butyldiphenylsilyl) group [see Wentland et al., "Selective Protection and Functionalization of Morphine...", *J. Med. Chem.* 43, 3558-3565 (2000)].

The invention claimed is:
1. A compound of formula I:

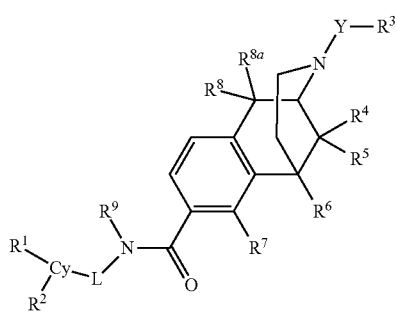

wherein
R$^1$ and R$^2$ are each independently selected from hydrogen, halogen, —OH, —CN, —CHO, —OCH$_3$, —OCH$_2$CH$_3$, —OCH(CH$_3$)$_2$, —NO$_2$, —COR$^{10}$, —COOR$^{10}$, —SO$_2$R$^{10}$, —CONR$^{10}$R$^{11}$, CSNR$^{10}$R$^{11}$, —CONR$^{10}$NR$^{11}$R$^{12}$, —CONR$^{10}$OR$^{11}$, —CONR$^{10}$((C (R$^{12}$)(R$^{13}$)$_t$CONR$^{10}$R$^{11}$, —CONR$^{10}$((C(R$^{12}$) (R$^{13}$)$_t$COOR$^{11}$, —C(=S)R$^{10}$, —C(=NOR$^{11}$)R$^{10}$, C(=NR$^{10}$)R$^{11}$, —SO$_2$NR$^{10}$R$^{11}$, heterocyclyl, optionally substituted lower alkyl, optionally substituted alkenyl, optionally substituted alkynyl, optionally substituted aryl, halo(C$_1$-C$_6$)alkyl, halo(C$_1$-C$_6$)alkoxy, and (C$_1$-C$_6$)alkylthio;

or, R$^1$ and R$^2$ together with the atoms to which they are attached, and a fragment selected from —OCH$_2$O—, or —OCH$_2$CH$_2$O—, form a ring, wherein when Cy is an aromatic group R$^1$ and R$^2$ cannot both be hydrogen;

wherein when Cy is an aromatic group R$^1$ and R$^2$ cannot both be halogen;

R$^3$ is chosen from hydrogen, C$_1$-C$_8$ hydrocarbon, heterocyclyl, aryl and hydroxyalkyl;

R$^4$ is chosen from hydrogen, hydroxyl, amino, lower alkoxy, C$_1$-C$_{20}$ alkyl and C$_1$-C$_{20}$ alkyl substituted with hydroxyl or carbonyl;

R$^5$ is lower alkyl;

R$^6$ is lower alkyl;

R$^7$ is chosen from hydrogen, NR$^{10}$R$^{11}$ and —OR$^{10}$; or together R$^4$, R$^5$, R$^6$ and R$^7$ may form from one, two, three, or four rings, said rings having optional additional substitution;

R$^8$ and R$^{8a}$ are both hydrogen or taken together R$^8$ and R$^{8a}$ are =O;

R$^9$ is chosen from hydrogen and lower alkyl;

R$^{10}$, R$^{11}$, R$^{12}$ and R$^{13}$ are each independently hydrogen, optionally substituted lower alkyl, optionally substituted alkenyl, optionally substituted alkynyl, optionally substituted aryl, hydroxyl, —NR$^{100}$R$^{101}$ or optionally substituted lower alkoxy, or R$^{10}$ and R$^{11}$, together with the nitrogen atom to which they are attached, form an optionally substituted fused carbocyclic or heterocyclic ring having from 5 to 7 ring members of which up to 3 can be heteroatoms selected from N, O and S;

t is 0, 1, 2, 3, 4, 5, or 6;

R$^{100}$ and R$^{101}$ are each independently hydrogen, optionally substituted lower alkyl, optionally substituted alkenyl, optionally substituted alkynyl, optionally substituted aryl, hydroxyl, or optionally substituted lower alkoxy, or R$^{100}$ and R$^{101}$, together with the nitrogen atom to which they are attached, form an optionally substituted fused carbocyclic or heterocyclic ring having from 5 to 7 ring members of which up to 3 can be heteroatoms selected from N, O and S;

Y is a direct bond or —(C(R$^{10}$)(R$^{11}$))q-, wherein q is 0, 1, 2, 3, 4 or 5;

L is a direct bond or —(C(R$^{10}$)(R$^{11}$))q-; and

Cy is Ar$^1$—B—Ar$^2$, wherein
  Ar$^1$ is absent, or an aryl or heteroaryl radical having from 1 to 4 N, O and/or S atoms, which may be unsubstituted or mono-, di- or trisubstituted by halogen, lower alkyl, alkenyl, alkynyl, cycloalkyl, —OR$^{10}$, —NR$^{10}$R$^{11}$, CN, —COR$^{10}$ or —COOR$^{10}$;
  B is a direct bond, —O—, —NR$^{10}$, —SO$_2$, or —(C(R$^{10}$) (R$^{11}$)s-, wherein s is 0, 1, 2, 3, 4 or 5; and
  Ar$^2$ is aryl or heteroaryl radical having from 1 to 4 N, O and/or S atoms, which may be unsubstituted or mono-, di- or trisubstituted by halogen, lower alkyl, alkenyl, alkynyl, cycloalkyl, —OR$^{10}$, —NR$^{10}$R$^{11}$, —CN, —COR$^{10}$ or —COOR$^{10}$, wherein when Cy is phenyl or biphenyl, R$_1$ is other than —OCH$_3$.

2. A compound of claim 1 wherein Cy is selected from:
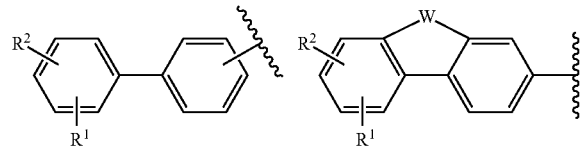
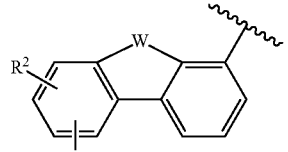
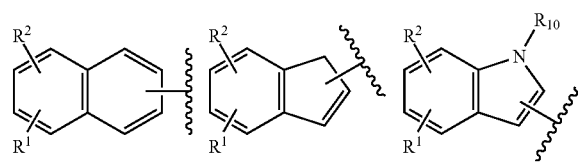
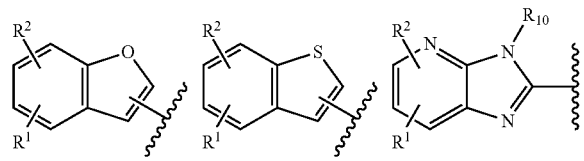
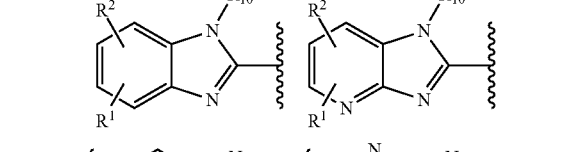
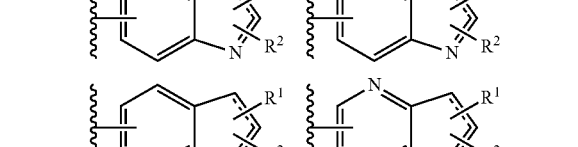
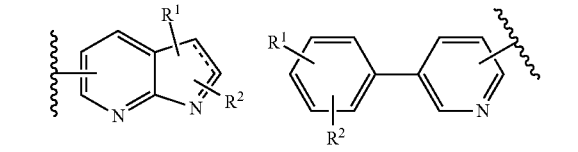
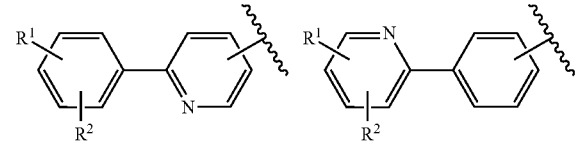
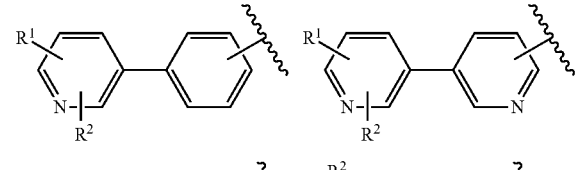
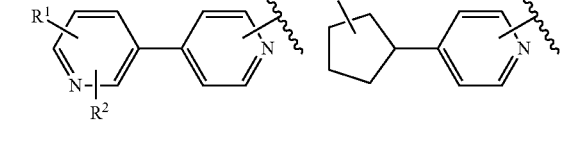
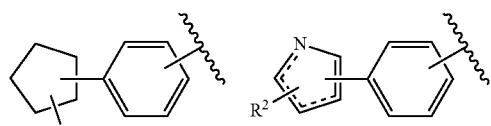
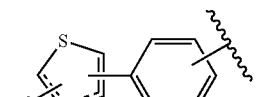
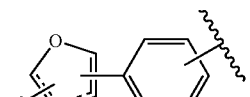
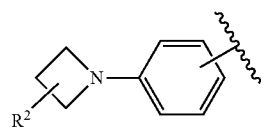
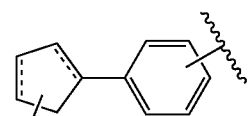
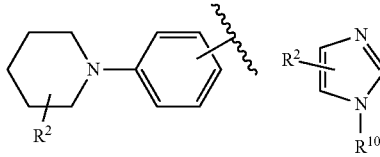
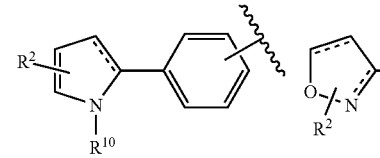
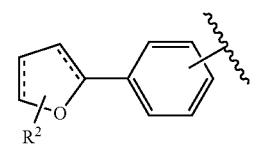
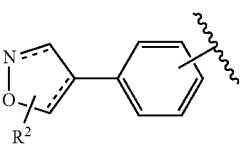
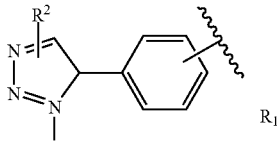
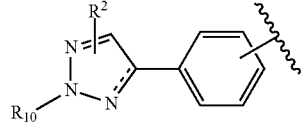
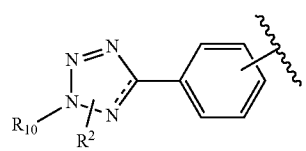
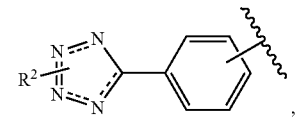
wherein W is selected from $[C(R^9)_2]_n$, $CR^8R^{8a}$, O, $NR^9$, S and $CR^9{=}CR^9$; and
n is 1, 2, 3, 4 or 5.

3. A compound of claim 1 of formula III-VI:

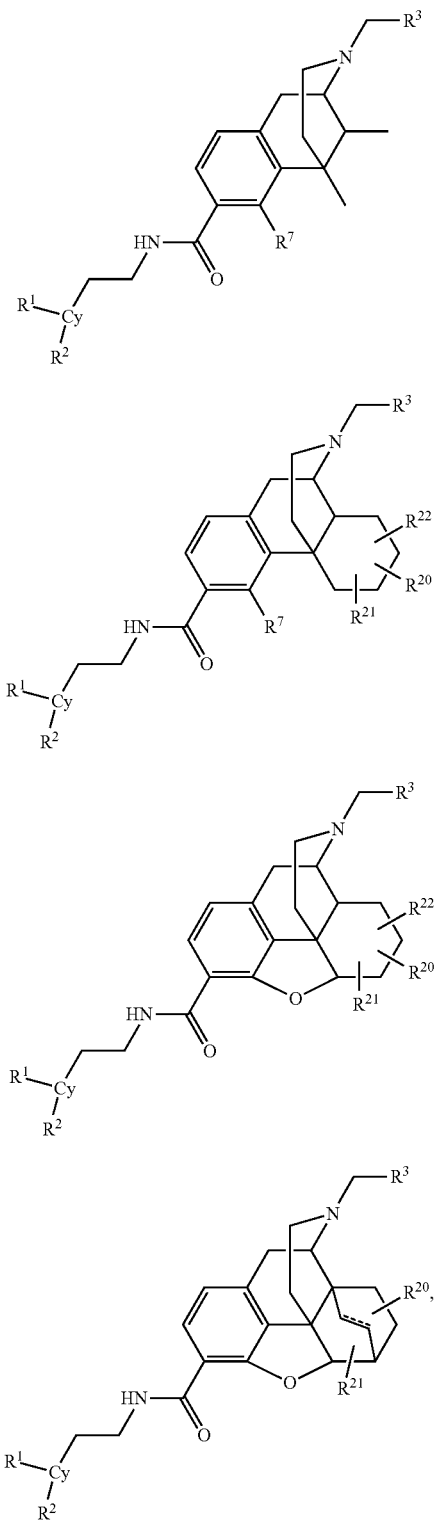

wherein, $R^{20}$, $R^{21}$ and $R^{22}$ are each chosen from hydrogen, hydroxyl, amino, lower alkoxy, $C_1$-$C_{20}$ alkyl and $C_1$-$C_{20}$ alkyl substituted with hydroxyl or carbonyl; or together, $R^{20}$, and $R^{21}$ with the carbon to which they are attached, form —CO, or —CS; or together, $R^{20}$, and $R^{21}$ with the carbon(s) to which they are attached, form a ring.

4. A compound according to claim 1 of formula:

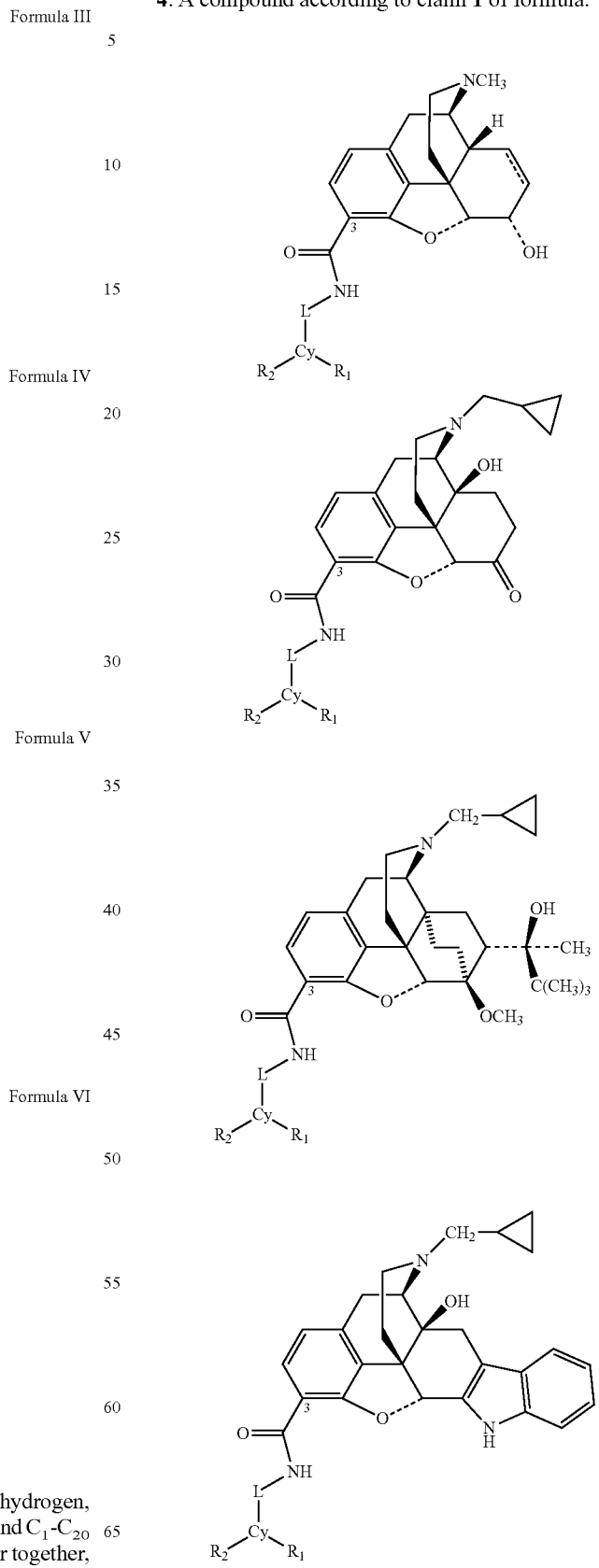

59
-continued
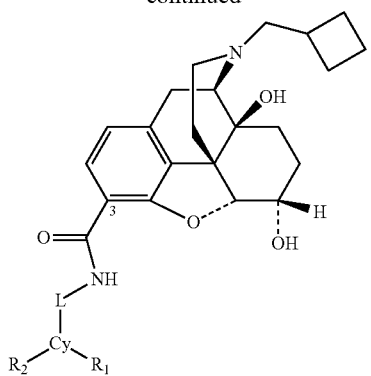
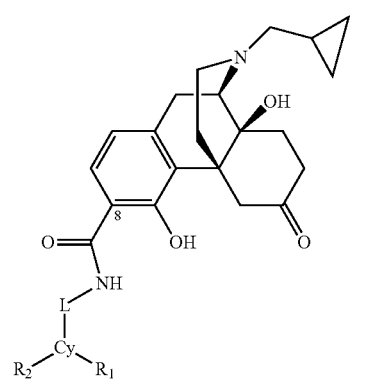
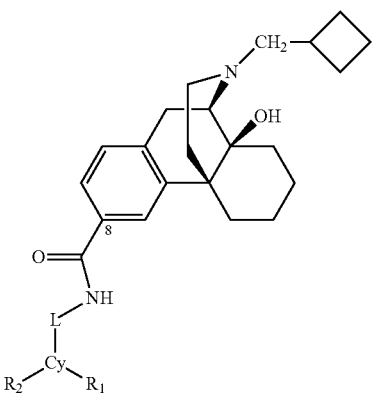
60
-continued
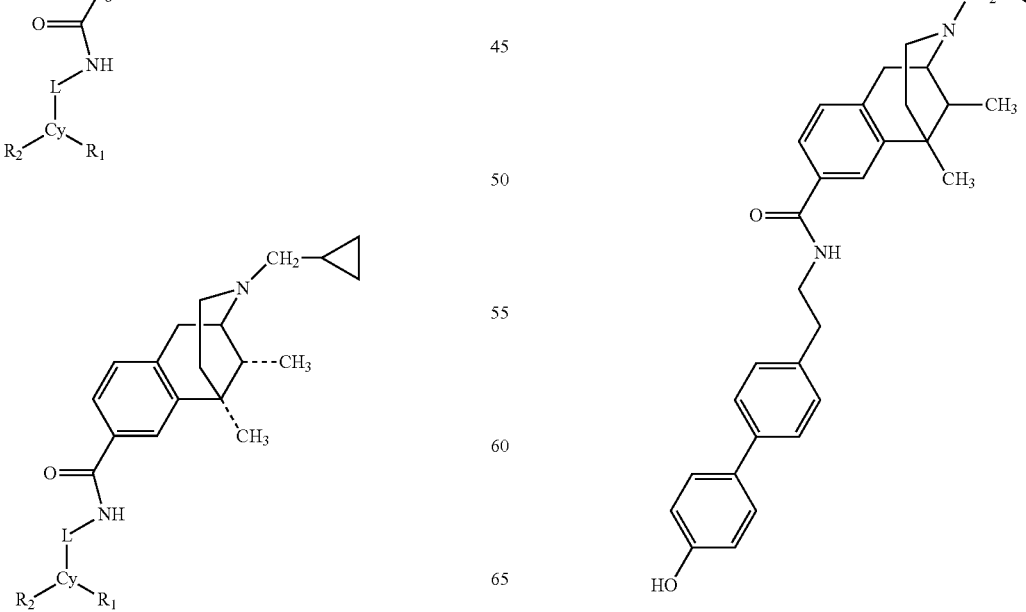
5. A compound according to claim 1 selected from Table 1:
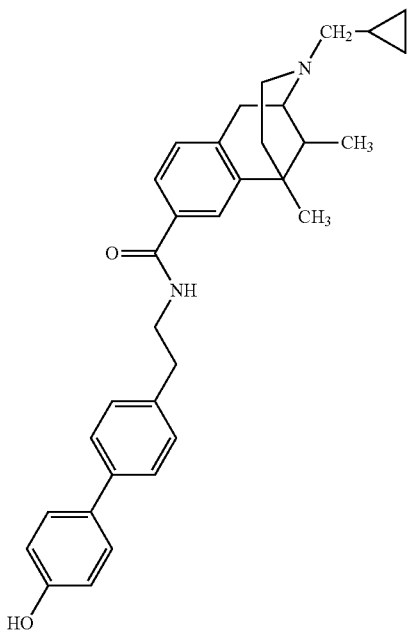

| No | Structure |
|---|---|
| 2 | 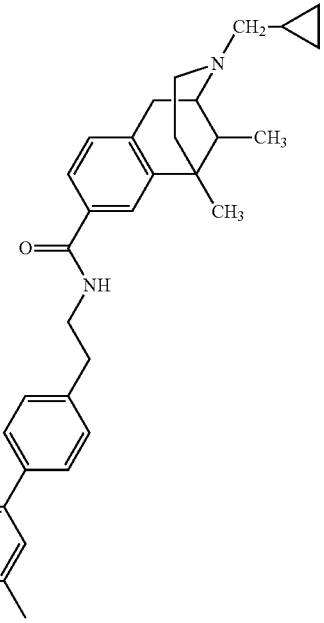 |
| 3 | 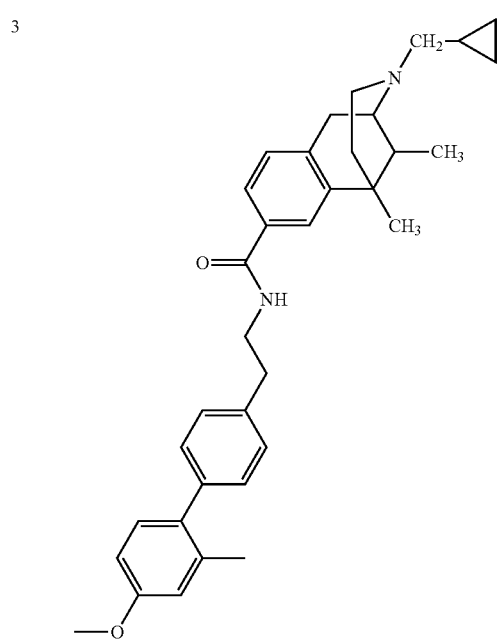 |
| No | Structure |
|---|---|
| 4 | |
| 5 | 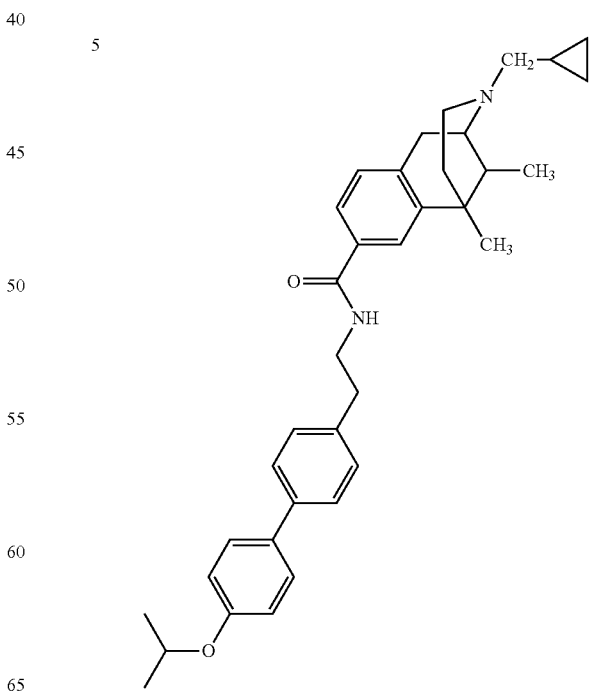 |

-continued
| No | Structure |
|---|---|
| 6 | 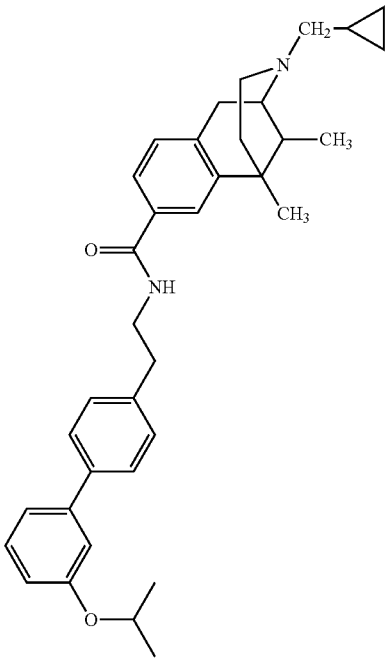 [SMILES: CC(C)Oc1cccc(-c2ccc(CCNC(=O)c3ccc4c(c3)C3(C)CCN(CC5CC5)C(C4)C3C)cc2)c1] |
| 7 | 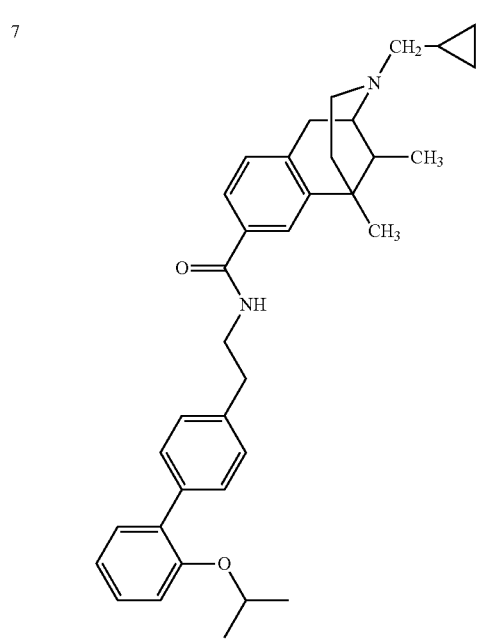 |
-continued
| No | Structure |
|---|---|
| 8 | 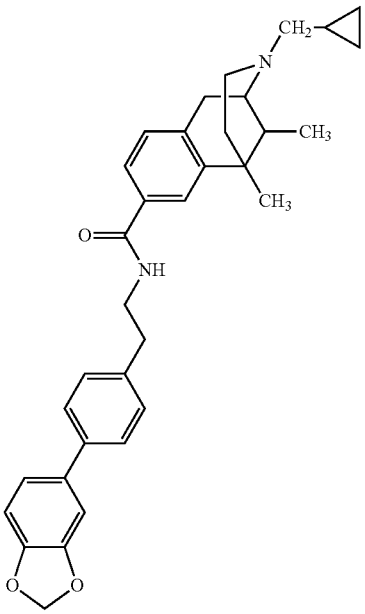 [SMILES: CC1C2Cc3ccc(C(=O)NCCc4ccc(-c5ccc6c(c5)OCO6)cc4)cc3C1(C)CCN2CC1CC1] |
| 9 | 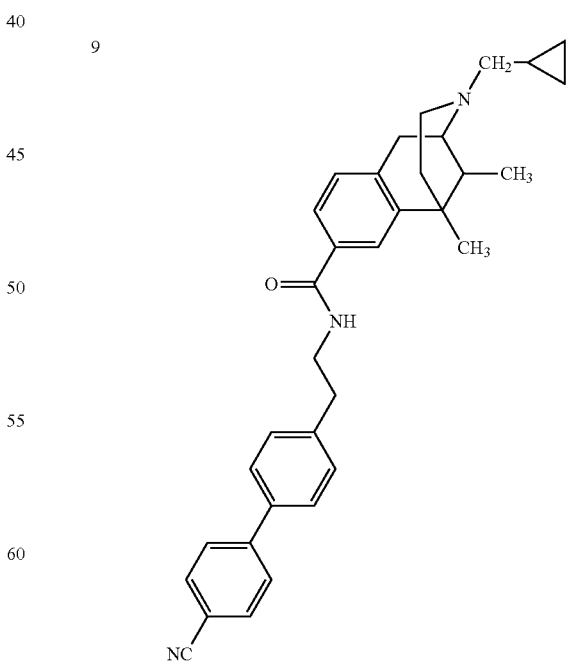 |

| No | Structure |
|---|---|
| 10 | |
| 11 | 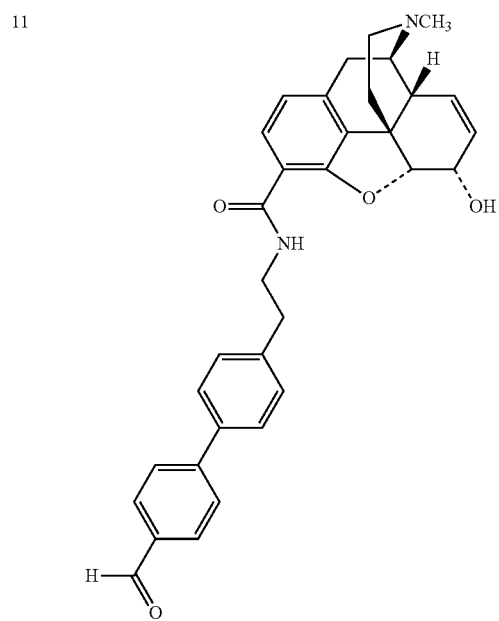 |
| No | Structure |
|---|---|
| 12 | |
| 13 | 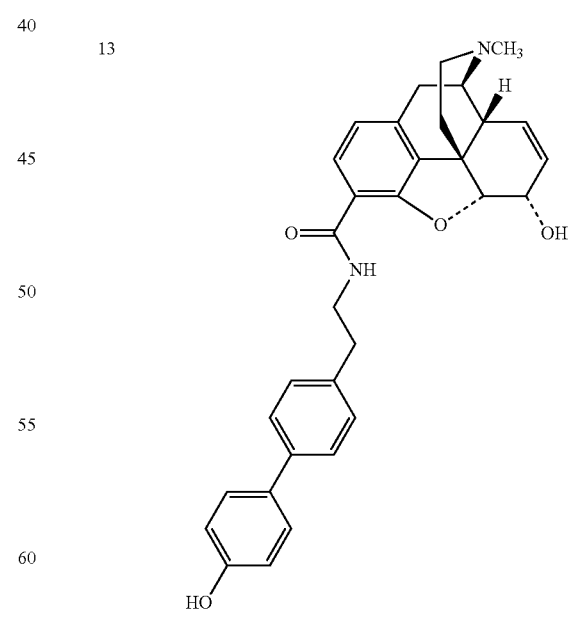 |

-continued
| No | Structure |
|----|-----------|
| 14 | 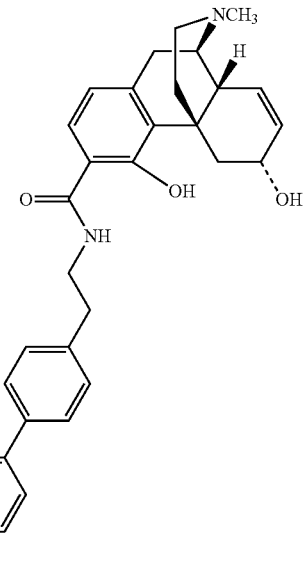 |
| 15 | 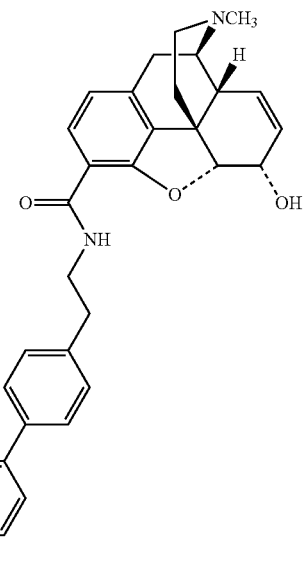 |
-continued
| No | Structure |
|----|-----------|
| 16 | 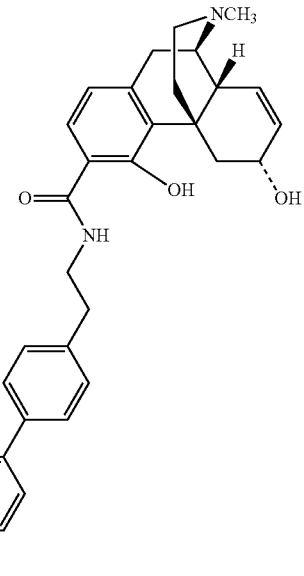 |
| 17 | 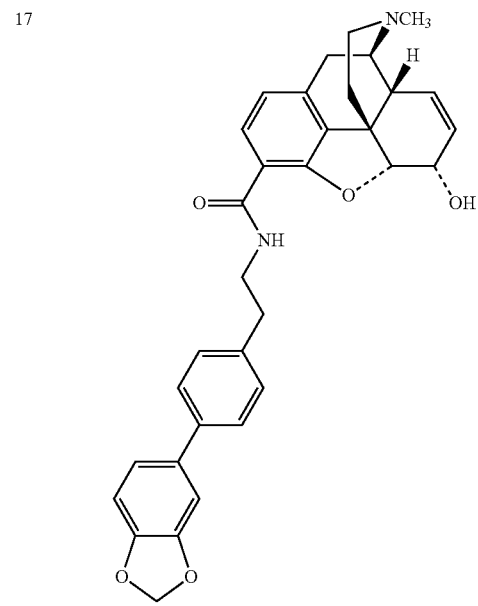 |

-continued
| No | Structure |
|---|---|
| 18 | 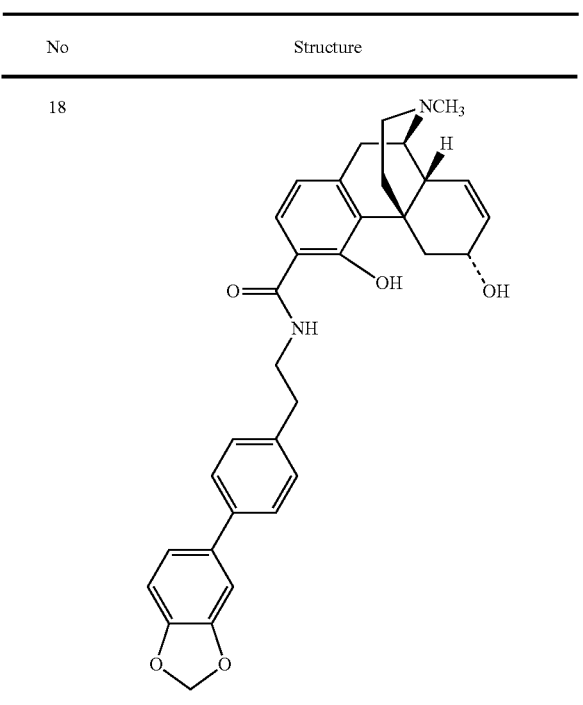 |
| 19 | 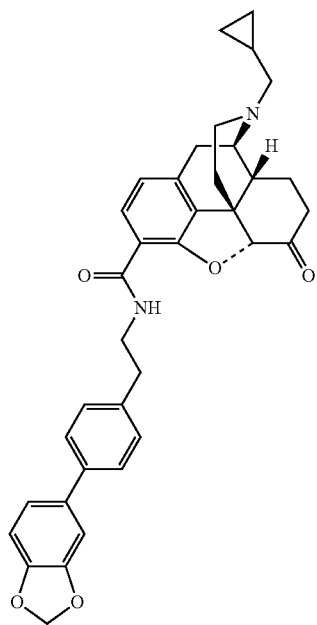 |
-continued
| No | Structure |
|---|---|
| 20 | 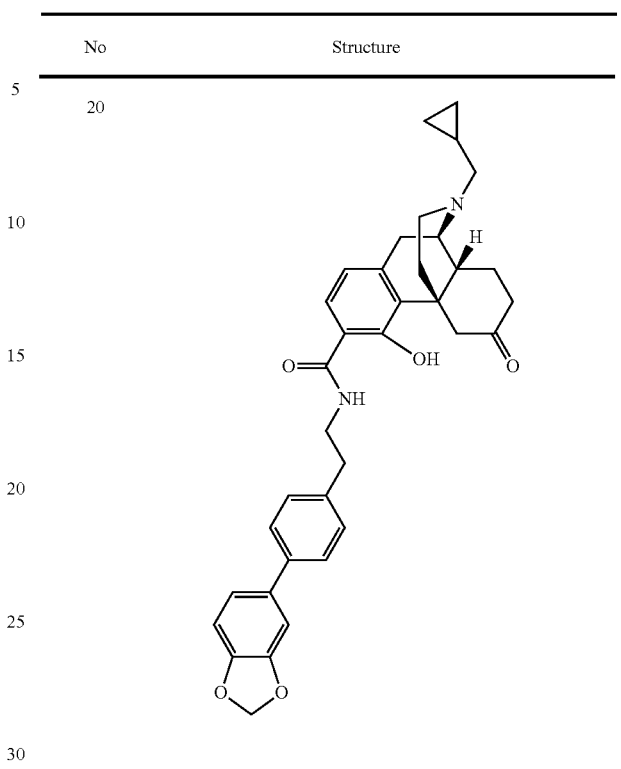 |
| 21 | |

-continued
| No | Structure |
|---|---|
| 22 | 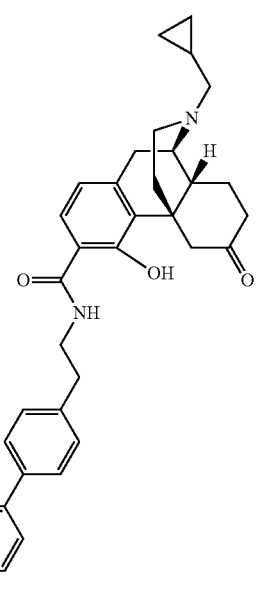 |
| 23 | 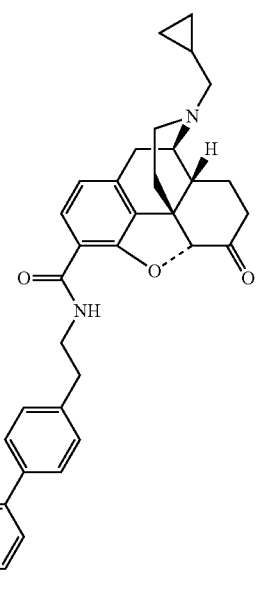 |
-continued
| No | Structure |
|---|---|
| 24 | 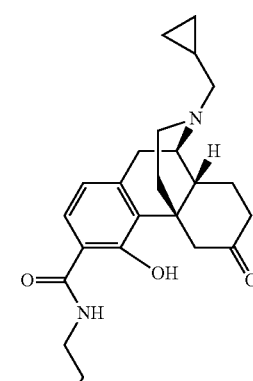 |
| 25 | 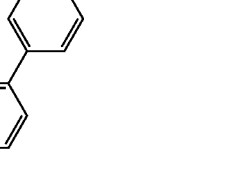 |

73
-continued
| No | Structure |
|---|---|
| 26 | 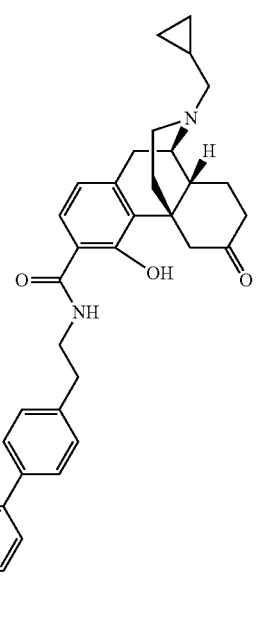 |
| 27 | 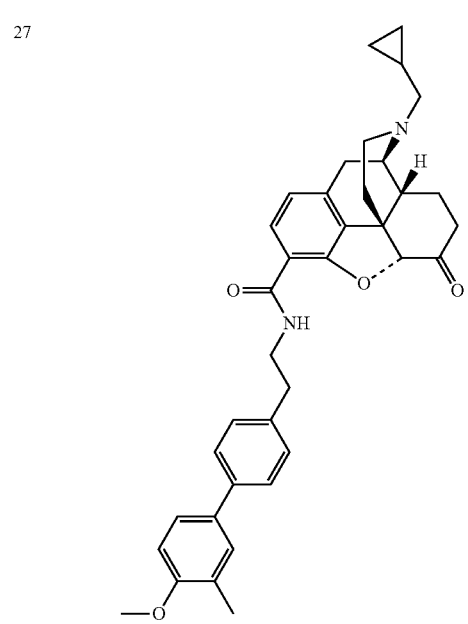 |
74
-continued
| No | Structure |
|---|---|
| 28 | 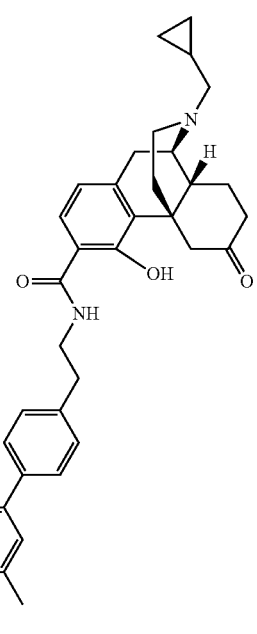 |
| 29 | 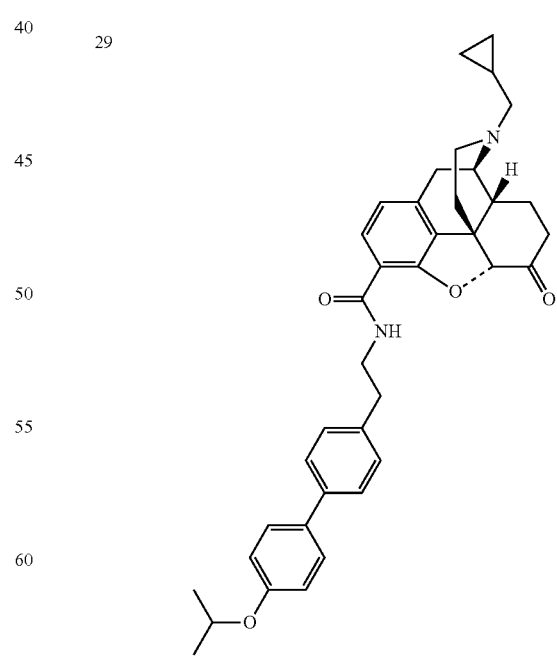 |

-continued
| No | Structure |
|---|---|
| 30 | |
| 31 | 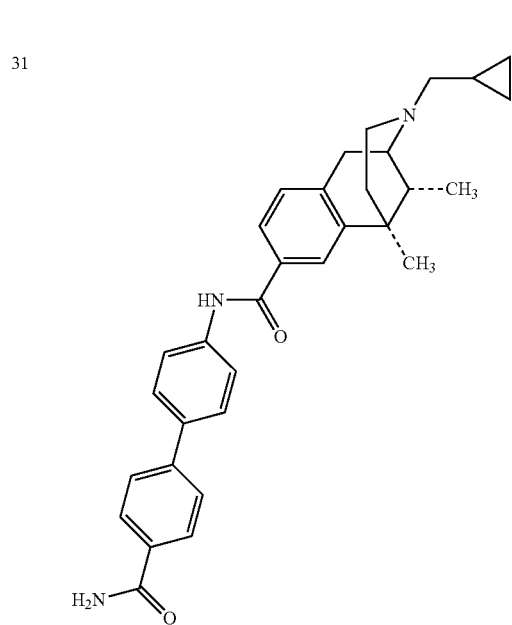 |
| No | Structure |
|---|---|
| 32 | |
| 33 | 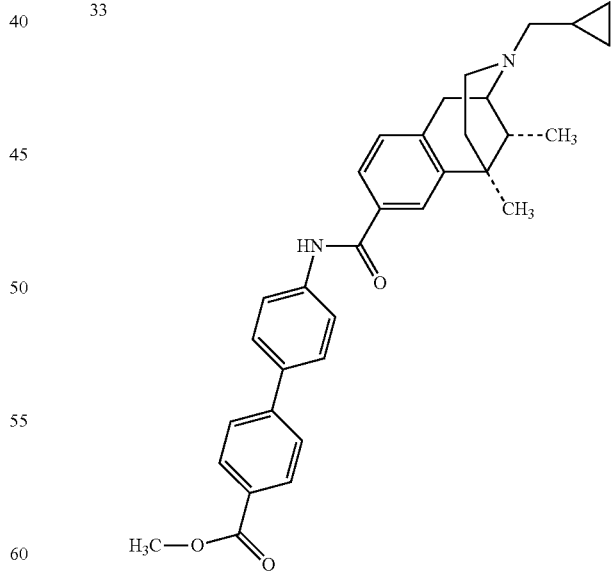 |

-continued
| No | Structure |
|----|-----------|
| 34 | 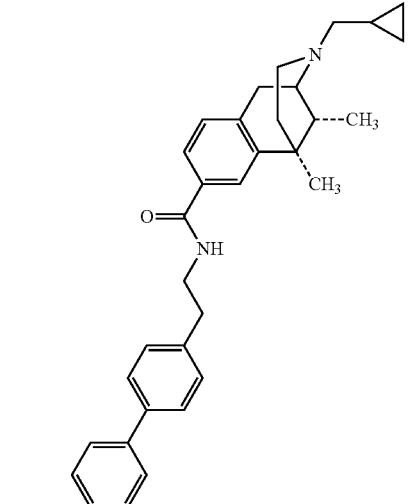 |
| 35 | 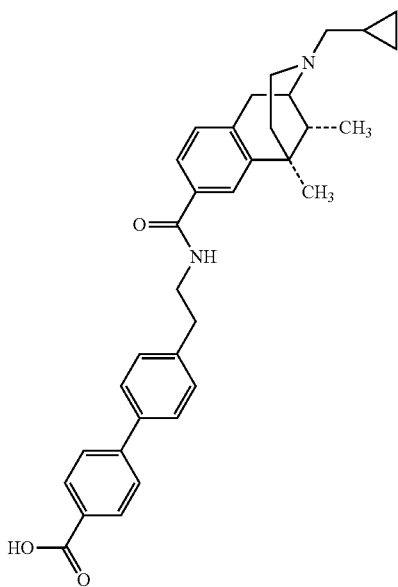 |
-continued
| No | Structure |
|----|-----------|
| 36 | 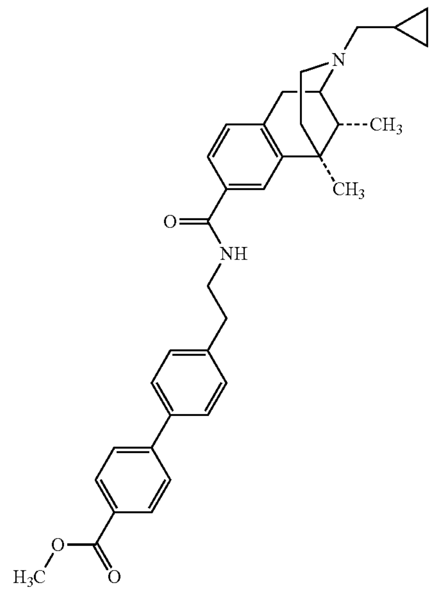 |
| 37 | 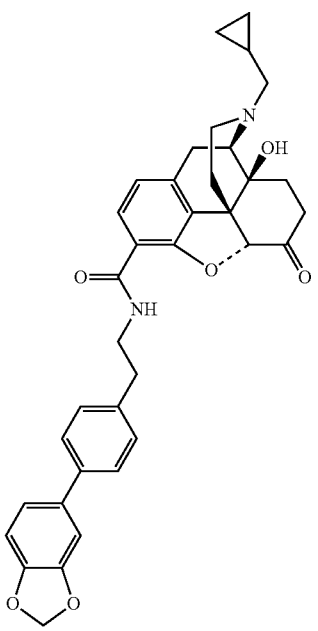 |

-continued
| No | Structure |
|----|-----------|
| 38 | 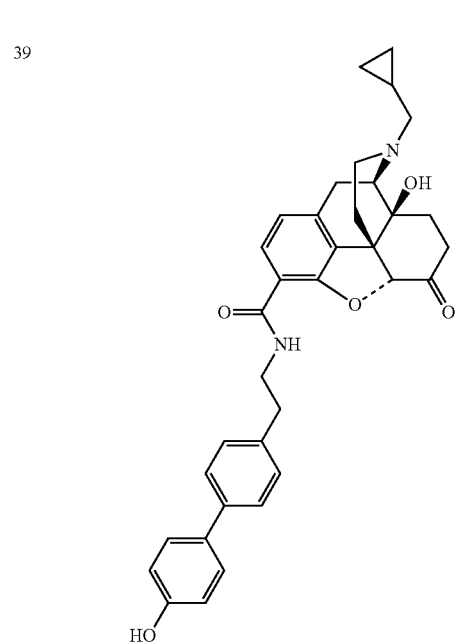 |
| 39 | 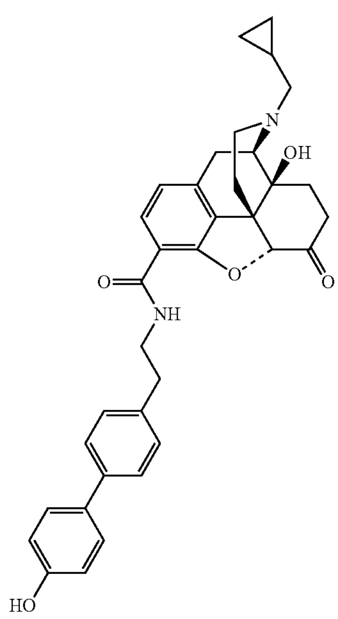 |
-continued
| No | Structure |
|----|-----------|
| 40 | 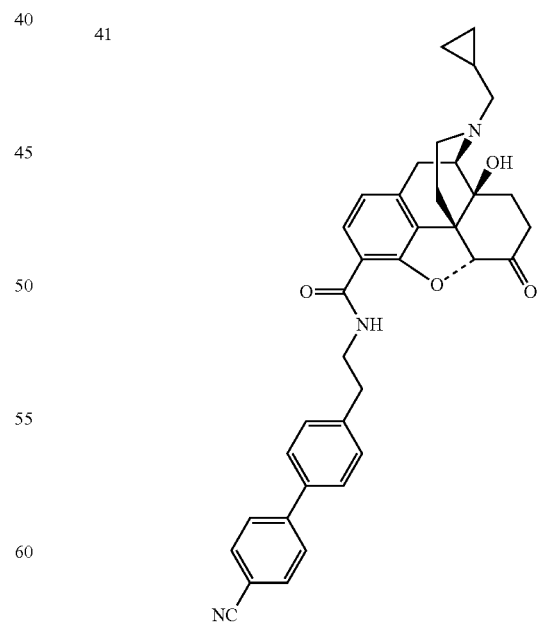 |
| 41 | 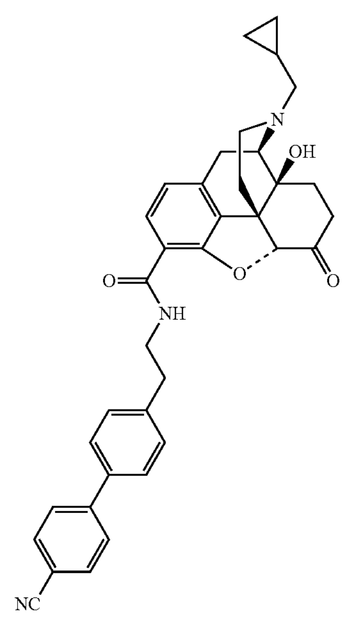 |

-continued

| No | Structure |
|---|---|
| 42 | (structure) |
| 43 | (structure) |
| 44 | (structure) |
| 45 | (structure) |

-continued

| No | Structure |
|---|---|
| 46 | 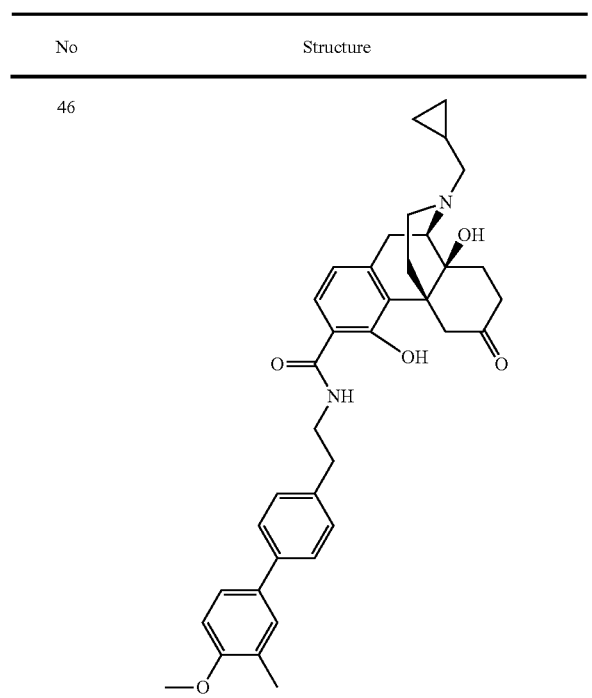 |
| 47 | 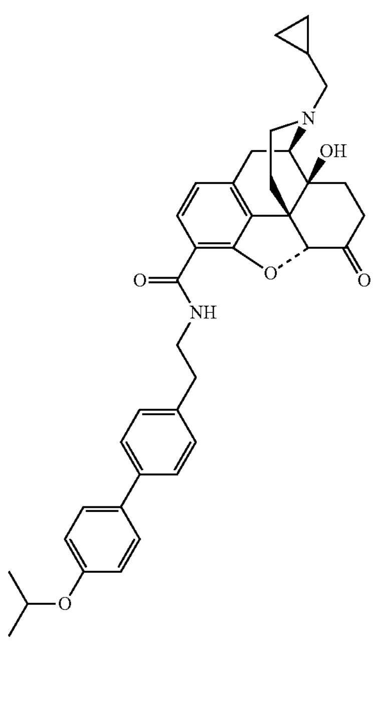 |

-continued

| No | Structure |
|---|---|
| 48 | 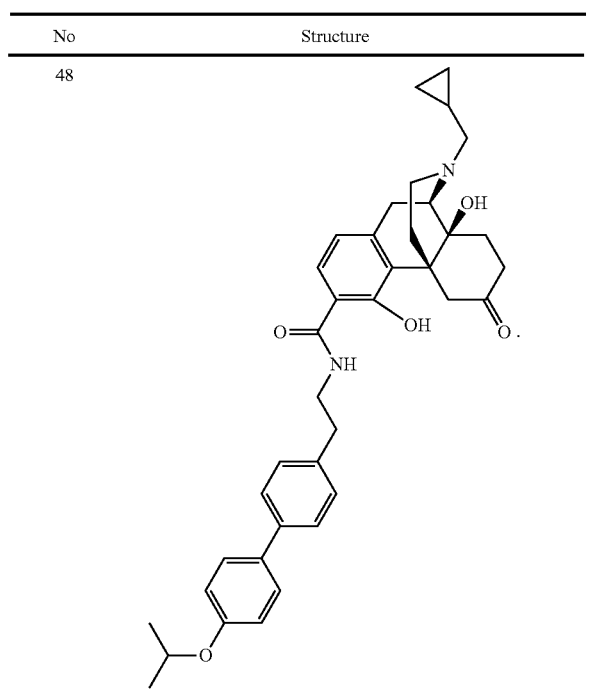 |

6. A compound according to claim 1 wherein Cy-R$^1$R$^2$ is of formula

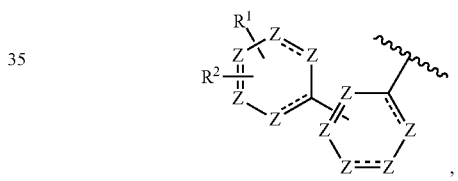

wherein Z is CR$^{10}$ or N, with the provisos that,
a) at the point of attachment of the distal ring to the proximal ring, Z must be C, and
b) at the points of attachment of R$^1$ and R$^2$, Z will be CR$^1$ and CR$^2$, respectively.

7. A compound according to claim 6 of formula wherein Cy-R$^1$R$^2$ is of formula:

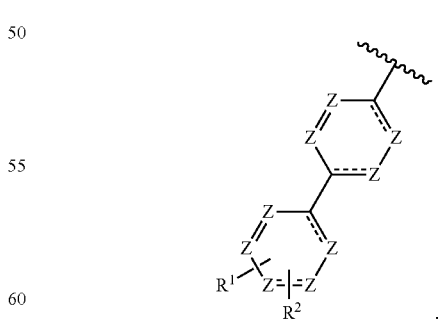

8. A compound according to claim 7 wherein one of R$^1$ and R$^2$ is in the para position relative to B and the other of R$^1$ and R$^2$ is hydrogen.

9. A compound according to claim 1, wherein Ar$^2$ is phenyl and one of R$^1$ or R$^2$ is in the para position relative to B.

10. A compound according to claim 9 wherein Cy-R¹R² is of formula:

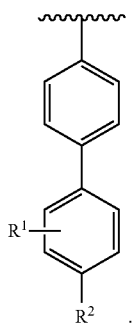

11. A pharmaceutical formulation comprising a compound according to claim 1 and a pharmaceutically acceptable carrier.

12. A method of treating pain, pruritis, diarrhea, irritable bowel syndrome, gastrointestinal motility disorder, obesity, respiratory depression, convulsions, coughing, hyperalgesia, inflammation, osteoarthritis and drug addiction associated with binding opioid receptors in a patient in need thereof, comprising the step of administering to said patient a composition comprising an effective amount of a compound according to claim 1.

13. A method according to claim 12, wherein the condition is pain and the composition further comprises an effective amount of an opioid.

14. A method according to claim 12, wherein the condition is osteoarthritis and the composition further comprises an effective amount of an opioid.

15. A compound of formula Ia:

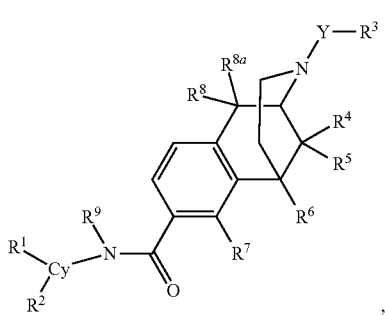

wherein
R¹ and R² are each independently selected from hydrogen, halogen, —OH, —CN, —CHO, —OCH₃, —OCH₂CH₃, —OCH(CH₃)₂, heterocyclyl, optionally substituted lower alkyl, optionally substituted alkenyl, optionally substituted alkynyl, optionally substituted aryl, halo($C_1$-$C_6$)alkyl, halo($C_1$-$C_6$)alkoxy, ($C_1$-$C_6$) alkylthio, —NO₂, —COR¹⁰, —SO₂R¹⁰, —CONR¹⁰R¹¹, —C(=S)R¹⁰, —C(=NOR¹¹)R¹⁰, C(=NR¹⁰)R¹¹ and —SO₂NR¹⁰R¹¹;
or, R¹ and R² together with the atoms to which they are attached, and a fragment selected from —OCH₂O—, or —OCH₂CH₂O—, form a ring,
with the proviso that R¹ and R² cannot both be hydrogen;
R³ is chosen from hydrogen, $C_1$-$C_8$ hydrocarbon, heterocyclyl, aryl and hydroxyalkyl;

R⁴ is chosen from hydrogen, hydroxyl, amino, lower alkoxy, $C_1$-$C_{20}$ alkyl and $C_1$-$C_{20}$ alkyl substituted with hydroxyl or carbonyl;
R⁵ is lower alkyl;
R⁶ is lower alkyl;
R⁷ is chosen from hydrogen, NR¹⁰R¹¹ and —OR¹⁰; or
together R⁴, R⁵, R⁶ and R⁷ may form from one to four rings, said rings having optional additional substitution;
R⁸ and R⁸ᵃ are both hydrogen or taken together R⁸ and R⁸ᵃ are =O;
R⁹ is chosen from hydrogen and lower alkyl;
R¹⁰ and R¹¹ are each independently hydrogen, optionally substituted lower alkyl, optionally substituted alkenyl, optionally substituted alkynyl, optionally substituted aryl, hydroxyl, —NR¹⁰⁰R¹⁰¹ or optionally substituted lower alkoxy, or
R¹⁰ and R¹¹, together with the nitrogen atom to which they are attached, form an optionally substituted fused carbocyclic or heterocyclic ring having from 5 to 7 ring members of which up to 3 can be heteroatoms selected from N, O and S;
R¹⁰⁰ and R¹⁰¹ are each independently hydrogen, optionally substituted lower alkyl, optionally substituted alkenyl, optionally substituted alkynyl, optionally substituted aryl, hydroxyl, or optionally substituted lower alkoxy, or
R¹⁰⁰ and R¹⁰¹, together with the nitrogen atom to which they are attached, form an optionally substituted fused carbocyclic or heterocyclic ring having from 5 to 7 ring members of which up to 3 can be heteroatoms selected from N, O and S;
Y is a direct bond or —(C(R¹⁰)(R¹¹)) q-, wherein q is 0, 1, 2, 3, 4 or 5; and
Cy is Ar¹—B—Ar², wherein
Ar¹ is absent, or an aryl or heteroaryl radical having from 1 to 4 N, O and/or S atoms, which may be unsubstituted or mono-, di- or trisubstituted by halogen, lower alkyl, alkenyl, alkynyl, cycloalkyl, —OR¹⁰, —NR¹⁰R¹¹, —CN, —COR¹⁰ or —COOR¹⁰;
B is a direct bond, —O—, —NR¹⁰, —SO₂, or —(C(R¹⁰)(R¹¹)s-, wherein s is 0, 1, 2, 3, 4 or 5; and
Ar² is aryl or heteroaryl radical having from 1 to 4 N, O and/or S atoms, which may be unsubstituted or mono-, di- or trisubstituted by halogen, lower alkyl, alkenyl, alkynyl, cycloalkyl, —OR¹⁰, —NR¹⁰R¹¹, —CN, —COR¹⁰ or —COOR¹⁰,
wherein when Cy is phenyl or biphenyl, R₁ is other than —OCH₃.

16. A compound of claim 15 wherein Cy is selected from:

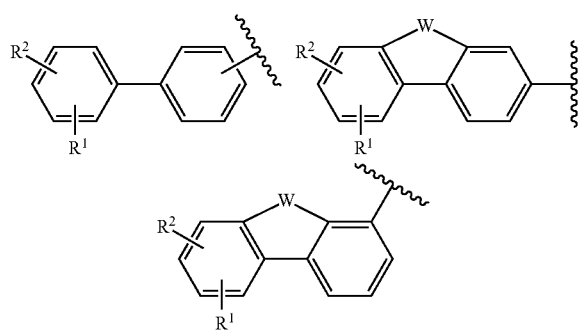

-continued

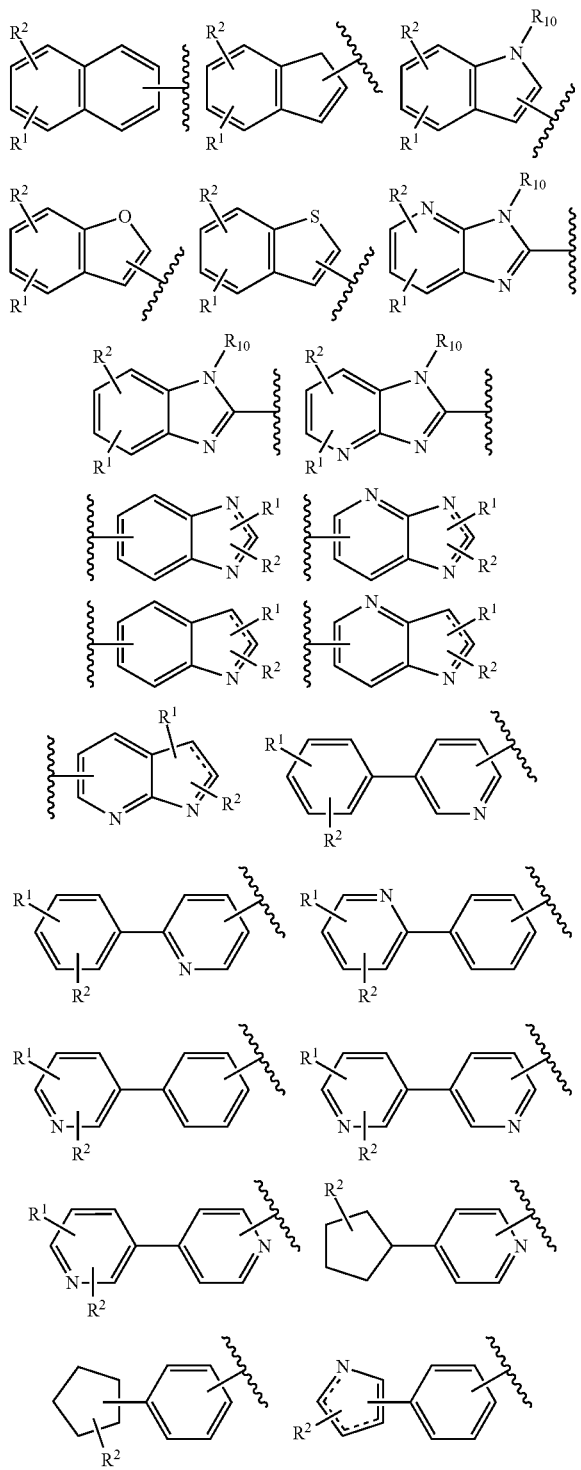
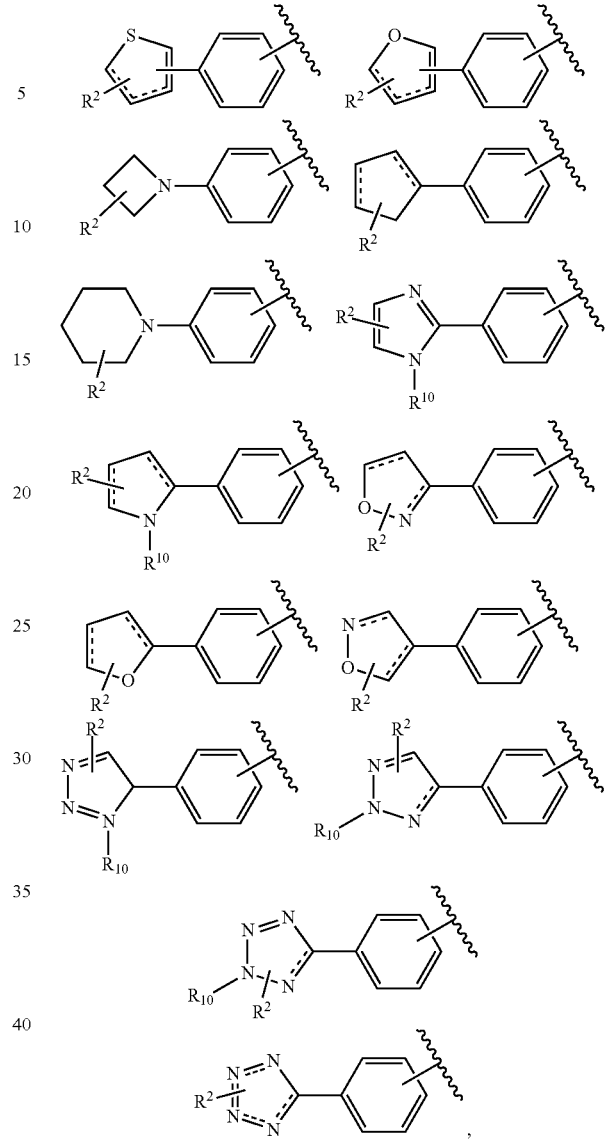

wherein W is selected from $[C(R^9)_2]_n$, $CR^8R^{8a}$, O, $NR^9$, S and $CR^9=CR^9$; and
n is 1, 2, 3, 4 or 5.

17. A compound according to claim 1 wherein said $R^{10}$ and $R^{11}$ are hydrogen.

18. A compound according to claim 1 wherein $R_1$ is —OH, —CHO, —CONH$_2$—CON(H)CH$_2$CONH$_2$, —CON(H)CH$_2$CH$_2$CONH$_2$, —CON(H)CH$_2$COOH, or —CON(H)CH$_2$CH$_2$COOH; or $R^1$ and $R^2$ together with the atoms to which they are attached forms a —OCH$_2$O— fused ring.

19. A compound according to claim 1 wherein $R_2$ is H.

* * * * *